(12) United States Patent
Albert et al.

US008078408B2

(10) Patent No.: US 8,078,408 B2
(45) Date of Patent: Dec. 13, 2011

(54) BRIDGED ELEMENT FOR DETECTION OF A TARGET SUBSTANCE

(75) Inventors: Fred Albert, Bozeman, MT (US); Brad Wright, Belgrade, MT (US)

(73) Assignee: The Procter & Gamble Company, Cincinnati, OH (US)

( * ) Notice: Subject to any disclaimer, the term of this patent is extended or adjusted under 35 U.S.C. 154(b) by 679 days.

(21) Appl. No.: 10/913,021

(22) Filed: Aug. 6, 2004

(65) Prior Publication Data

US 2005/0074871 A1    Apr. 7, 2005

Related U.S. Application Data

(60) Provisional application No. 60/493,142, filed on Aug. 6, 2003.

(51) Int. Cl.
    *G01N 33/48* (2006.01)
(52) U.S. Cl. .......................................................... 702/19
(58) Field of Classification Search ...................... 702/19
    See application file for complete search history.

(56) References Cited

U.S. PATENT DOCUMENTS

| 5,763,768 | A | 6/1998 | Henderson et al. |
| 5,866,328 | A | 2/1999 | Bensimon et al. |
| 6,251,660 | B1 * | 6/2001 | Muir et al. ................. 435/287.2 |
| 6,333,157 | B1 * | 12/2001 | Miller-Jones et al. ............ 435/6 |
| 7,112,452 | B2 | 9/2006 | Cho et al. |
| 2002/0090649 | A1 * | 7/2002 | Chan et al. ...................... 435/7.1 |
| 2002/0154029 | A1 * | 10/2002 | Watters et al. ........... 340/870.07 |
| 2003/0027187 | A1 | 2/2003 | Strick et al. |
| 2003/0110844 | A1 | 6/2003 | Struckmeier et al. |
| 2004/0248282 | A1 * | 12/2004 | Sobha et al. ............... 435/287.2 |
| 2005/0125014 | A1 | 6/2005 | Duluco et al. |

FOREIGN PATENT DOCUMENTS

| CN | 1415963 | 5/2003 |
| EP | 1306449 A2 | 5/2003 |
| WO | WO-03/057091 A1 | 7/2003 |
| WO | WO-03057901 A2 | 7/2003 |
| WO | WO-2005038459 A2 | 4/2005 |
| WO | WO-2005038459 A3 | 4/2005 |

OTHER PUBLICATIONS

Lee et al., "Direct DNA Hybridization Detection Based on the Oligonucleotide-Functionalized Conductive Polymer," Anal. Chem. (2001) vol. 73, pp. 5629-5632.*
"International Search Report and Written Opinion, for Application No. PCT/US2004/025708, date mailed Jul. 27, 2005", 18 Pages.
Bach, H. J., et al., "Specific detection of the gene for the extracellular neutral protease of Bacillus cereus by PCR and blot hybridization", *Applied and Environmental Microbiology*, vol. 65, No. 7, (1999), 3226-3228.
Birnboim, H. C., et al., "A rapid alkaline extraction procedure for screening recombinant plasmid DNA", *Nucleic Acids Res.* 7(6), (Nov. 24, 1979), 1513-23.

Bucior, I., et al., "Carbohydrate-carbohydrate interaction provides adhesion force and specificity for cellular recognition", *J Cell Biol.*, 165(4), (May 24, 2004), 529-37.
Connolly, B. A., "Chemical synthesis of oligonucleotides containing a free sulphydryl group and subsequent attachment of thiol specific p", *Nucleic Acids Research*, 13(12), (Jun. 25, 1985), 4485-502.
Kumar, A., et al., "A simple method for introducing a thiol group at the 5'-end of synthetic oligonucleotides", *Nucleic Acids Research*, 19(16), (Aug. 25, 1991), 4561.
Naismith, J. H., et al., "Refined structure of concanavalin A complexed with methyl α-D-mannopyranoside at 2.0 Å resolution and comparison with the saccharide-free structure", *Acta Cryst.*, D50, (1994), 847-858.
Rees, William A., et al., "Betaine Can Eliminate the Base Pair Composition Dependence of DNA Melting", *Biochemistry*, vol. 32, (1993),137-144.
Rief, M., et al., "Reversible Unfolding of Individual Titin Immunoglobulin Domains by AFM", *Science* 276(5315), (1997), 1109-1112.
Southern, E. M., "Detection of Specific Sequences Among DNA Fragments Separated by Gel Electrophoresis", *Journal of Molecular Biology*, vol. 98. (1975), 503-517.
Zimmermann, R. H., et al., "DNA stretching on functionalized gold surfaces", *Nucleic Acids Res.*, 22(3), (Feb. 11, 1994), 492-497.
"Chinese Patent Application No. 200480025562.6, First Office Action mailed Dec. 21, 2007", 11 pgs.
"European Patent Application No. 04816802.5, Response filed Jun. 18, 2007 to Communication mailed Dec. 8, 2006", 8 pgs.
"European Patent Application No. 04816802.5, First Examination Report mailed Dec. 8, 2006", 4 pgs.
"Indian Patent Application No. 426/CHENP/2006, First Examination Report mailed Dec. 27, 2007", 9 pgs.
Marmur, J., "A Procedure for the Isolation of Deoxyribonucleic Acid from Micro-organisms", *J. Mol. Biol.*, 3, (1961), 208-218.
"Chinese Application Serial No. 200480025562.6, Office Action mailed Jan. 18, 2008", 15 pgs.
"Chinese Application Serial No. 200480025562.6, Office Action mailed Jun. 25, 2008", 6 pgs.
"Chinese Application Serial No. 200480025562.6, Office Action mailed Sep. 26, 2008", 10 pgs.
"Chinese Application Serial No. 200480025562.6, Office Action mailed Oct. 13, 2008", 14 pgs.
"Chinese Application Serial No. 200480025562.6, Office Action Response filed May 5, 2008", 15 pgs.
"Chinese Application Serial No. 200480025562.6, Office Action mailed Sep. 26, 2008", 10 pgs.
"Chinese Application Serial No. 200480025562.6, Office Action mailed Oct. 13, 2008", 14 pgs.
"Chinese Application Serial No. 200480025562.6, Office Action Response filed May 5, 2008", 15 pgs.

(Continued)

*Primary Examiner* — Jerry Lin
(74) *Attorney, Agent, or Firm* — Brent M. Peebles; Kim W. Zerby

(57) ABSTRACT

Physical changes resulting from an association between a template molecule and a target molecule are detected by monitoring changes in the template molecule. Exemplary changes include a change in a physical dimension or stiffness of the template molecule, a change in electrical conductivity of the template molecule and a change in the energy required to dissociate the target molecule and the template molecule. The magnitude of the change is indicative of the specific identity of the target molecule.

38 Claims, 12 Drawing Sheets

OTHER PUBLICATIONS

"Chinese Application Serial No. 200480025562.6, Office Action Response filed Aug. 21, 2008", 14 pgs.

"European Application Serial No. 04816802.5, Office Action mailed Aug. 29, 2006", 7 pgs. "European Application Serial No. 04816802.5, Response filed Jun. 18, 2007", 9 pgs.

"India Application Serial No. 00426/CHENP/2006, Office Action mailed Dec. 4, 2008", 2 pgs.

"India Application Serial No. 00426/CHENP/2006, Response filed Jun. 2, 2008", 10 pgs.

"International Application Serial No. PCT/US2004/025708, Search Report mailed Jul. 27, 2005".

"International Application Serial No. PCT/US2004/025708, Written Opinion mailed Jul. 27, 2005", 9 pgs.

"India Application Serial No. 00426/CHENP/2006, Office Action dated Jul. 30, 2008", 3 pgs.

200480025562.6, "Chinese Application No. 200480025562.6, Office Action mailed Jul. 15, 2009", 5 pgs.

* cited by examiner

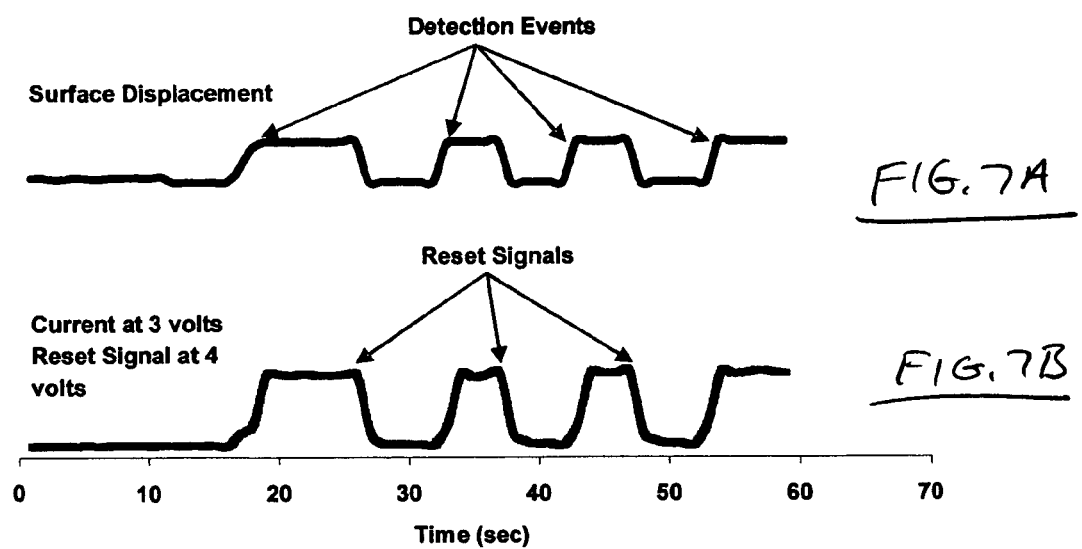

BRIDGED ELEMENT FOR DETECTION OF A TARGET SUBSTANCE

CROSS-REFERENCE TO RELATED APPLICATIONS

This document claims the benefit of priority, under 35 U.S.C. Section 119(e), to U.S. Provisional Patent Application Ser. No. 60/493,142, entitled "METHOD AND BIO-ELECTRONIC DEVICE FOR RAPID DETECTION OF ANALYTES SUCH AS BIOLOGICAL AGENTS," by Fred G. Albert et al., filed on Aug. 6, 2003, which is incorporated herein by reference.

TECHNICAL FIELD

This document pertains generally to sensor devices, and more particularly, but not by way of limitation, to detection and analysis of a target substance.

BACKGROUND

Previous efforts to detect analytes, such as biological agents, pathogens, bacteria, viruses, fungi, molecules and toxins are relatively cumbersome, time-consuming, and require significant technical expertise to operate. For example, one technique generally requires the incubation of samples on Petri plates over an extended period of several days. Another technique involves the use of dyed antibodies selected to identify the presence of specific pathogenic bacteria.

In addition, some systems require that the target biological molecules undergo an amplification procedure which is prone to errors and requires a high level of technical skill. Furthermore, amplification sometimes cannot determine the concentration of a target biological agent and are not practical for use in the field.

Some systems fail to detect natural or engineered changes in biological agents, are known to generate false positive errors and are sensitive to testing conditions. Some devices for the detection of biological molecules (such as DNA sequences or proteins) require a large number of target molecules to operate effectively. Accordingly, the target molecules must be amplified, and in some instances tagged which prevents further use of the template molecules.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIGS. 7A and 7B illustrate measured parameters as a function of time.

DETAILED DESCRIPTION

Figure 1:
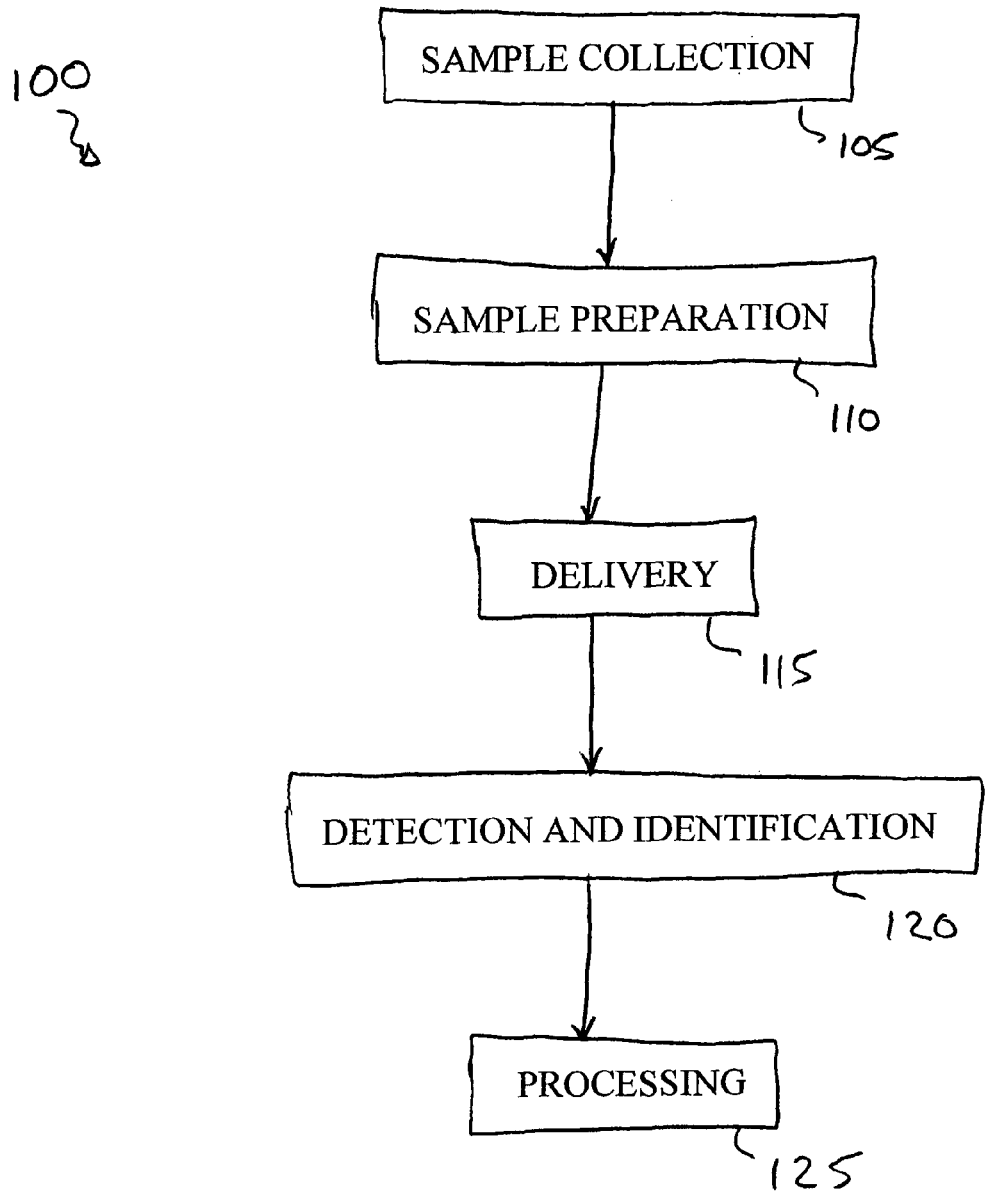
FIG. 1 illustrates a flow chart for a method of detecting a target molecule.

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. The detailed description, therefore, is not to be taken in a limiting sense, and the scope of various embodiments is defined only by the appended claims, along with the full range of equivalents to which such claims are entitled. Such embodiments of the inventive subject matter may be referred to herein, individually or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This document is intended to cover any and all adaptations, or variations, or combinations of various embodiments. Combinations of the above embodiments, and other embodiments not specifically described herein, will be apparent to those of skill in the art upon reviewing the above description.

Introduction

Molecules are affected by changes in their environment. For example, a single stranded deoxyribonucleic acid (ssDNA) will respond to the introduction of its complementary ssDNA. Hybridization of one DNA strand with its complementary strand results in a reduction in overall length, as well as a change in DNA conductive properties. The changes are directly proportional to the fidelity of match between the two DNA strands with even a single nucleotide mismatch having a measurable effect. Analysis of the changes permits identification of various pathogens and allows differentiating between specific strains.

In one example, a microelectromechanical (MEMS) structure is used to measure molecular changes associated with hybridization. For example, a mobile element in a MEMS chip is bridged by a selected single-strand DNA fragment. A complementary fragment is detected and identified based on a measurement of the deflection of the element and a measurement of conductivity resulting from hybridization. In one example, signal processing is used to interpret the hybridization events as detection and identification. The correlation of length and conductivity change to DNA strand homology is used to discriminate between known and variant pathogens, and between benign and virulent strains.

In addition, a voltage applied after hybridization causes the pathogen DNA strand, or target molecule, to be released from the template molecule. The current at which the target molecule releases can also provide information to identify the target molecule. In addition, by releasing the target molecule, the sensor can be prepared for an additional detection event. Furthermore, the integrity of the sensor is tested by conducting a low-level current through the template molecule prior to a sensing event to verify continuity. In one example, an array of DNA-bridged MEMS sensors allows simultaneous multiplexed detection of numerous viral or bacterial pathogens, or enables the measurement of concentration of a single pathogen.

In addition, changes in the resonance of the template molecule are used for identifying a sample that binds to the template molecule. In one example, a movable end of a cantilever is bridged to a structure by a template molecule. The resonance frequency of the cantilever system (with the template molecule bridge) will change upon hybridization of the sample with the template molecule. The degree of homology can be determined by the magnitude and direction of the shift in amplitude or frequency.

Exemplary Method

FIG. 1 illustrates exemplary procedure 100 for detecting and identifying a target substance. The target substance, in one example, includes a single strand DNA fragment.

As used herein, the target molecule and the template molecule are coined terms and the molecules are related in the manner of their binding together. Accordingly, a particular sensor uses a first ssDNA strand as a template molecule and a second ssDNA strand is a target molecule, another sensor can use the first ssDNA strand as the target molecule and the second ssDNA strand as the template molecule.

Other combinations of binding partners are also contemplated. For example, either the template molecule or the target molecule can include nucleic acid molecules (e.g. oligonucleotides, including ss-DNA or RNA referred to as ss-RNA), proteins and carbohydrates. A template molecule comprising a single strand of DNA may hybridize with a complementary strand of DNA to form a double stranded DNA (ds-DNA). In addition, a template molecule including a protein may bind to a target molecule that also includes a protein (through a protein-protein recognition), a nucleic acid (through protein-nucleic acid recognition) or a carbohydrate (through protein-carbohydrate recognition). In addition, a template molecule including nucleic acid may bind to a target molecule including a nucleic acid using DNA (through nucleic acid-nucleic acid recognition) or a carbohydrate (through nucleic acid-carbohydrate recognition). Furthermore, a template molecule including a carbohydrate may bind to a target molecule including a carbohydrate (through carbohydrate-carbohydrate recognition). In general, template molecule-target molecule combinations can be described as a lock-and-key mechanism that allows certain molecules to bind only with other molecules.

At 105, the sample to be analyzed is collected. The sample, which potentially includes the target molecule, can be in a gas, liquid or solid form. At the sample is prepared for analysis, which, in one example, includes filtering of the sample. At 115, the sample is delivered to the sensor for analysis. Sample delivery, in one example, includes routing the sample using a microfluidic pump, valve, channel, reservoir or other structure. At 120, the sample is introduced to one or more sensors for possible detection and identification. In various examples, detection and identification include monitoring for a change in length or position, a change in a force, a change in electrical conductivity or resistivity, determining a signal level for disbonding a sample from the template molecule and determining a shift in resonance. At 125, the collected data is processed to detect and identify the sample. Processing the data, in various examples, includes comparing an output signal with stored data where the stored data includes a look-up table which correlates a target molecule with a template molecule.

Other procedures are also contemplated. For example, a sensor integrity test may be performed before exposing the sensor to the sample by monitoring various parameters.

Exemplary Cantilever Sensor

Figure 2:
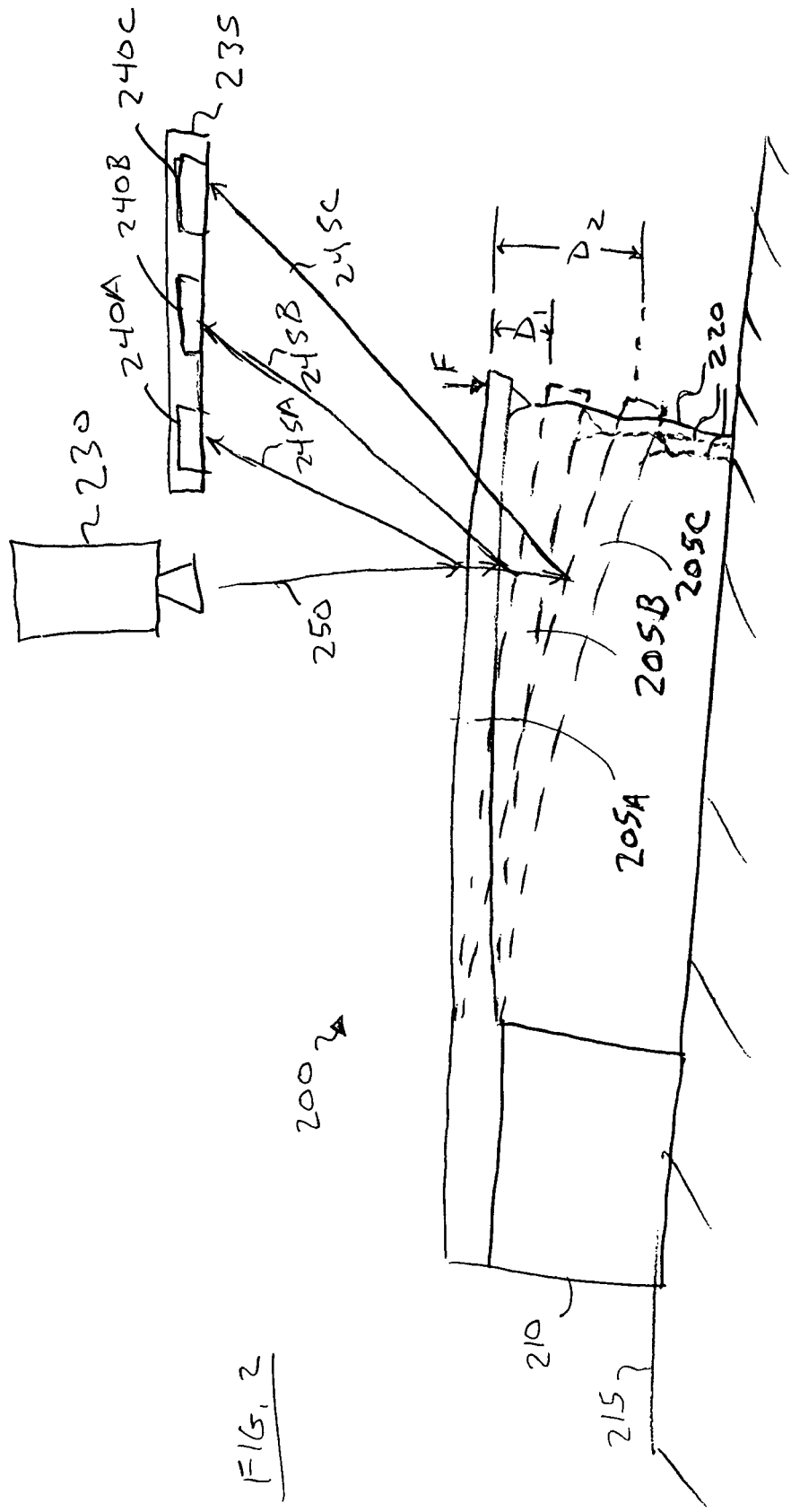
FIG. 2 illustrates a cantilever detector.

FIG. 2 illustrates sensor 200 according to one example. Substrate 215 provides a structure or reference stage upon which the cantilever is fabricated. Base 210 is affixed to one end of cantilever 205A and elevates cantilever 205A above substrate 215. In one example, cantilever 205A has dimensions of approximately 200 µm in length by 20 µm in width and 1 µm in thickness. A portion of template molecule 220 is affixed to a free end of cantilever 205A.

The figure illustrates template molecule 220 as a linear element having one end bonded to the free end of cantilever 205A and another end bonded to a portion of substrate 215. The space between cantilever 205A and substrate 215 is bridged by template molecule 220.

In the figure, template molecule 220 is shown at a time where no complementary binding partner has bonded and cantilever 205A is shown in a relaxed or unloaded state. Alternative positions for cantilever 205A are illustrated in dotted lines. Cantilever 205B, for example, is illustrated at a time when a binding partner has associated with template 220. Cantilever 205B has been displaced by distance D1 below the position shown by cantilever 205A. Template molecule 220 is associated with a binding partner of low affinity. Cantilever 205C illustrates a time when a different binding partner has associated with template 220. Cantilever 205C has been displaced by distance D2 below the position shown by cantilever 205A. Cantilever 205C represents the case when template molecule 220 is associated with a binding partner with greater affinity than the binding partner represented with cantilever 220B.

Displacement of cantilever 205A is detected, in one example by an optical detection system. In the figure, optical source 230 projects light beam 250 on a surface of cantilever 205A which is reflected, as shown by ray 245A, and detected by cell 240A of optical sensor 235. Cantilever 205B reflects light, as shown by ray 245B which is detected by cell 240B and cantilever 205C reflects light, as shown by ray 245C which is detected by cell 240C. Sensor 235 is illustrated as having three cells, however, more or less are also contemplated. In one example, optical source 230 includes a laser or other source of collimated light.

Other means for detecting displacement or resonance of cantilever 205A are also contemplated. In one example, a piezoelectric element provides an electrical signal as a function of deflection of cantilever 205A. The piezoelectric element includes a piezoelectric material that is bonded to, or integrated with, a surface of cantilever 205A, base 210, or other structure.

In one example, a measure of capacitance is used to determine displacement or resonance. For example, a conductive layer of a cantilever structure serves as a capacitor plate. Capacitance between the conductive layer of the cantilever and another conductor varies with the distance between the conductors. Thus, a measure of capacitance can provide displacement and resonance data. In various examples, the conductive layer of the cantilever is electrically isolated from other conductive layers of the cantilever.

In one example, a magnetic or electric field is used to determine the displacement or resonance of a cantilever structure. Relative motion between a magnet and a conductor provides a signal used to determine displacement or resonance. In addition, a strain gauge affixed to a cantilever provides displacement and resonance information.

Exemplary Cantilever Structure

Figure 3:
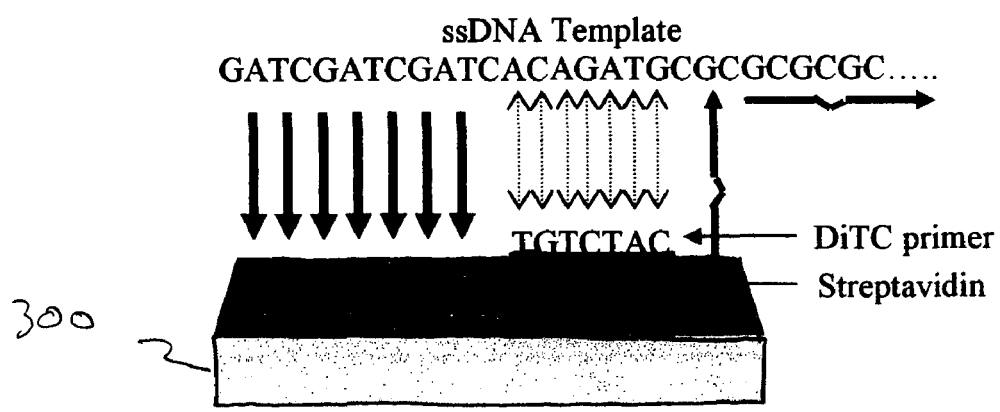
FIG. 3 illustrates a portion of a cantilever structure. (SEQ ID NO:12)

FIG. 3 illustrates an example of a sensor structure fabricated using Directed Template Circuitry (DiTC) construction. Directed template circuitry uses microelectromechanical systems, self assembled monolayers (SAMs), and DNA hybridization. Using lithography, thin films of various materials, including metals such as silver (Ag), chromium (Cr), gold (Au) and carbon, are patterned in micron size dimensions. Self assembled monolayers allow selectively immobilizing template molecules on a MEMS surface. In addition, proteins and other biomolecules can be immobilized onto surfaces such as gold using SAMs. Moreover, target analytes can be detected using amperometric methods and SAMs on electrodes.

In one embodiment of the directed template circuit, SAMs technology is used to apply a monolayer of the protein streptavidin on gold which is layered on chromium. Streptavidin is immobilized on the gold electrode surface based upon binding the protein to a biotinylated disulde monolayer on the gold surface.

Figure 8:
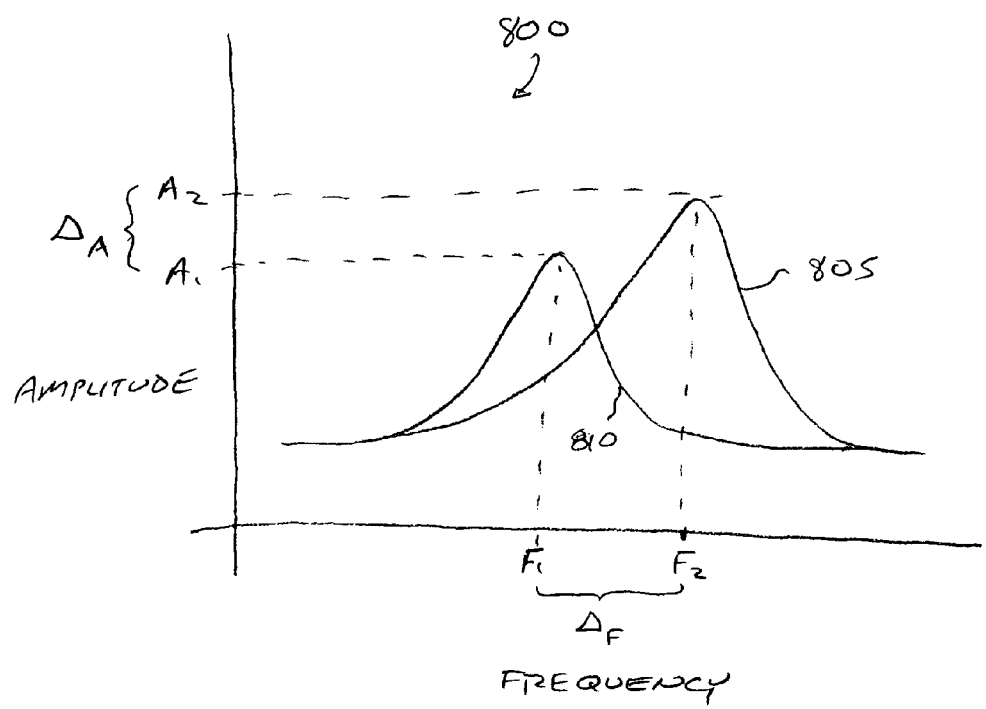
FIG. 8 illustrates a shift in resonance.

The same biotin based chemistry is then used to bind between approximately 20 and 100 base oligonucleotides primers specifically designed and synthesized to hybridize to the single-stranded DNA template bridge as shown in FIG. 8. The directed template circuitry primers direct the orientation and positioning of the ssDNA template bridge, i.e. the left-hand primer.

In one example, a single-strand DNA (ssDNA) template is bound using oligonucleotides primers in a manner that bridges an electronic MEMS based circuit. Hybridization to target DNA derived from the microorganism being identified causes a reduction in distance between cantilever arms.

Manufacturing of MEMS microchip devices using directed template circuitry entails, briefly, a gel photopolymerization technique to produce micromatrices of polyacrylamide gel pads separated by a hydrophobic glass surface. In one example, DNA oligonucleotides are applied to the gel pads and tested for proper positioning and orientation by fluorescence microscopy and exonuclease digestion.

Other methods can be used to attach the template molecule to the contact points in a manner that aligns the template molecule for detection and identification of a target molecule. For example, bonds established using gold-Streptavidin and sulfur group/biotin are also contemplated.

In one example, the primers are designed and synthesized to hybridize to a template molecule comprising a single stranded DNA molecule. Furthermore, the primers are arranged and oriented so that the template molecule will have a desired orientation and position. More particularly, the primers ensure that a selected portion (at or towards a first end) of the template molecule is bound to one surface of the cantilever and that a selected portion (at or towards a second end) of the template molecule is bound to another surface of the cantilever. In various examples, the ends of the template molecule are keyed to a specific portion of the cantilever structure (one way alignment) or not keyed (two way alignment)

Performance—Displacement

In one example, the strength of a DNA strand, and the length, is dependent upon base composition, sequence and the environment. A measurable biophysical phenomenon occurs when a single strand of DNA interacts with its complementary strand. In particular, the average free reduction in DNA length upon hybridization with its complements is approximately 40%. DNA nucleotide sequence and composition can be correlated with structural and other biophysical parameters.

Figure 4:
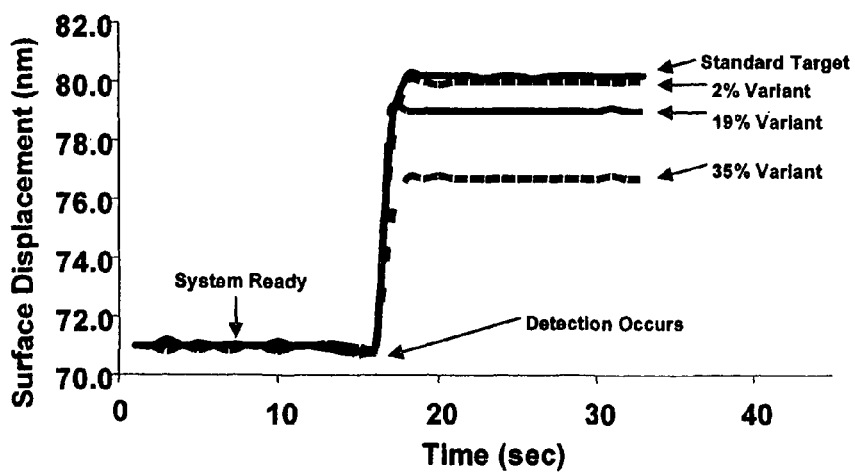
FIG. 4 illustrates a graph of displacement as a function of time.

FIG. 4 illustrates a relationship between force amplitude and displacement of a surface of cantilever 205A. For a particular cantilever, the measured performance can be used to identify a complementary binding partner. If a cantilever is exposed to a sample molecule that is not a completely complementary, then results will be different.

FIG. 4 graphically illustrates the strength of a biological molecule for one example. For the data presented, a molecule is tethered between the cantilever tip and a substrate. The tethering is accomplished by adding a functional group to the ends of the template ssDNA for attachment to the cantilever on one end of the sequence and to the substrate at the other end. Exemplary combinations include gold-Thiol bonds and biotin-streptavidin bonds.

Analysis of data to establish the molecular tensile strength is presented in the figure. In one example, the sensor structure is fabricated such that the template molecule is held in slight tension, however, a neutral or near zero tension is also contemplated. With the template molecule held in such a manner, a binding partner is introduced. For a template molecule of ssDNA, a suitable binding partner is the complementary ssDNA strand. The subsequent binding (or hybridization) of the template molecule with the target molecule provides a measurable change in a physical parameter or characteristic. The cantilever is able to detect (and measure) displacement and the change in length of the molecule due to hybridization.

The figure illustrates cantilever displacement relative to hybridization of a template ssDNA with a target ssDNA. As noted, the cantilever deformed by approximately 10.2 nm after exposing the template ssDNA with a genetically matching (or complementary) target ssDNA. This experimental approach was repeated on more than 100 different biological molecules.

In the figure, standard target represents a complementary ssDNA strand with 100% homology with the template molecule (strand). Other targets are illustrated at 2%, 19% and 38% variant from the 100% homologous complementary ssDNA strand. As used herein, the term variant denotes a target ssDNA containing random base pair substitutions relative to the 100% homologous complementary ssDNA strand.

The gradations noted in the figure illustrate that variant ssDNA molecules are also detectable and identifiable using the present system.

Exemplary Dual Cantilever Detector

Figure 5A:
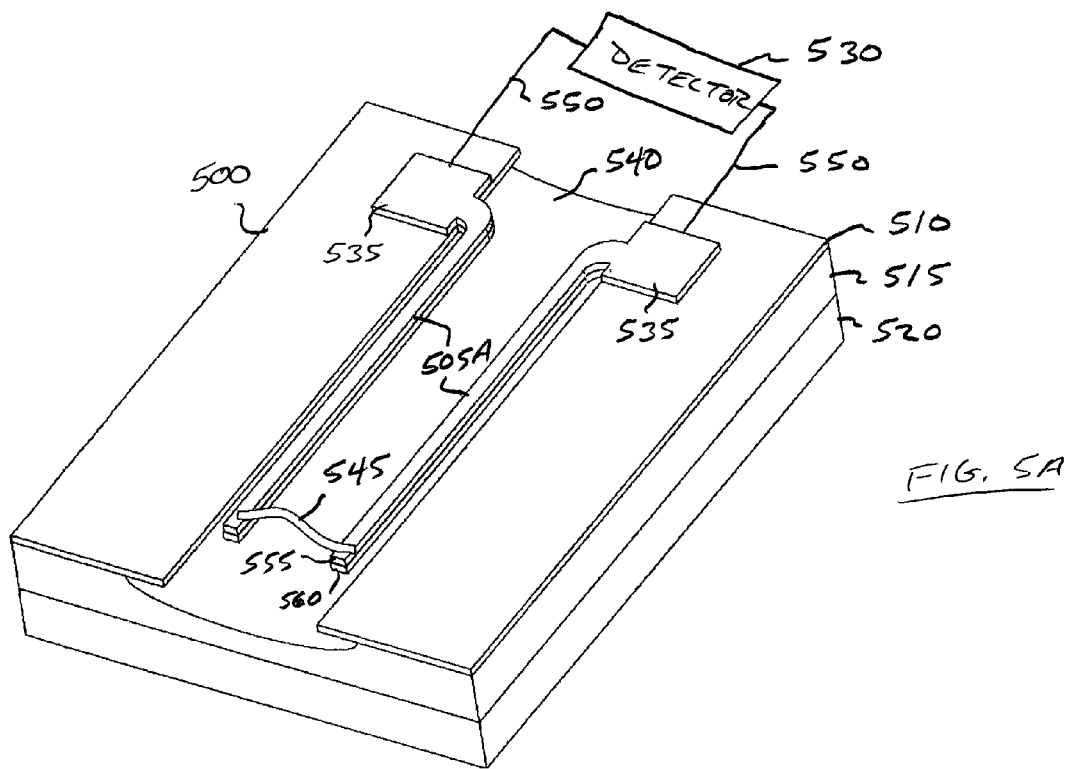
FIGS. 5A and 5B illustrate a cantilever detector system.
Figure 5B:
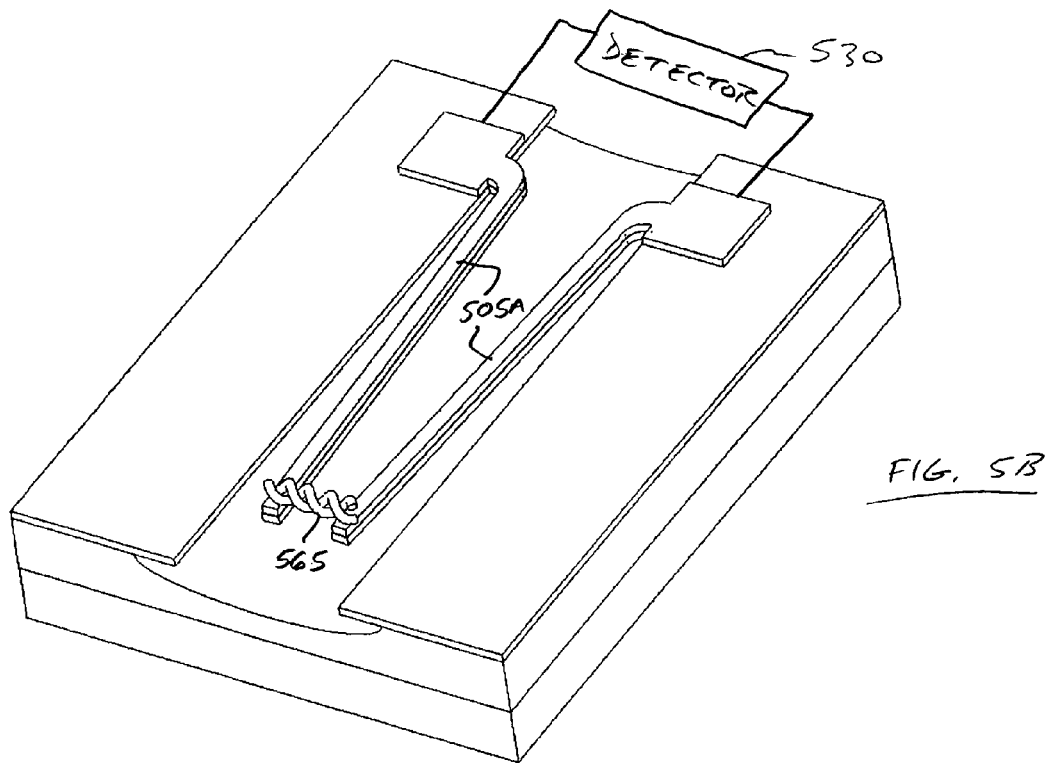

FIGS. 5A and 5B illustrate views of cantilever based sensor 500. FIG. 5A illustrates template molecule 545 bridging, or linking, the free ends of dual cantilevers 505A. Cantilevers 505A are electrically coupled to detector circuit 530 via conductors 550 and connection plates 535 disposed at stabilized ends of cantilevers 505A. Connection plates 535 are bonded to layer 510 which is disposed atop layers 515 and layer 520. Layers 510, 515 and 520, in one example, are comprised of Si3N4, Si, Si3N4 each having a thickness of approximately 50 nm, 150 nm and 250 nm, respectively. Cantilevers 505A are suspended above sample channel 540 formed in layer 515. Cantilevers 505A, in one example, are formed of layer 555 (gold) and layer 560 (chromium) having thicknesses of approximately 40 nm and 5 nm, respectively.

In FIG. 5A, cantilevers 505A are bridged by a template molecule of ssDNA 545 under little or no tensile forces. Detector circuit 530, in one example, provides an electrical current to detect the level of conductivity. It will be appreciated that conductivity is the reciprocal of resistance and in one example, a resistance is determined. In one example, an impedance value is determined. In FIG. 5B, bridge 565 represents a hybridized dsDNA formed by the combination of the template molecule (ssDNA) and the target molecule (ssDNA). As illustrated in FIG. 5B, cantilevers 505A are convergently deflected. Detector circuit 530 generates a measurement of conductivity and upon hybridization of the dsDNA strand, reflects a measured increase in conductivity.

In various examples, a test circuit and a reset circuit are provided in detector circuit 530. The test circuit is configured to provide a current to template molecule 545 to establish that the template molecule is properly affixed to the cantilever arms. For example, a series combination of a current source, sensor and a resistor will indicate an expected current flow if the sensor and template molecule are properly configured. Deviations from an expected current level may indicate that the template molecule or the sensor is not properly configured for sample testing.

A reset circuit of the detector circuit includes a driving circuit for disbonding the target molecule from the template molecule in preparation for another detection and identification event. In one example, this entails providing a ramping voltage to the template molecule and monitoring for a peak current. In one example, this entails providing a ramping current to the template molecule and monitoring for a peak voltage. The peak voltage, or current, will coincide with a denaturing or disassociating event of the template molecule and the target molecule.

Figure 6:
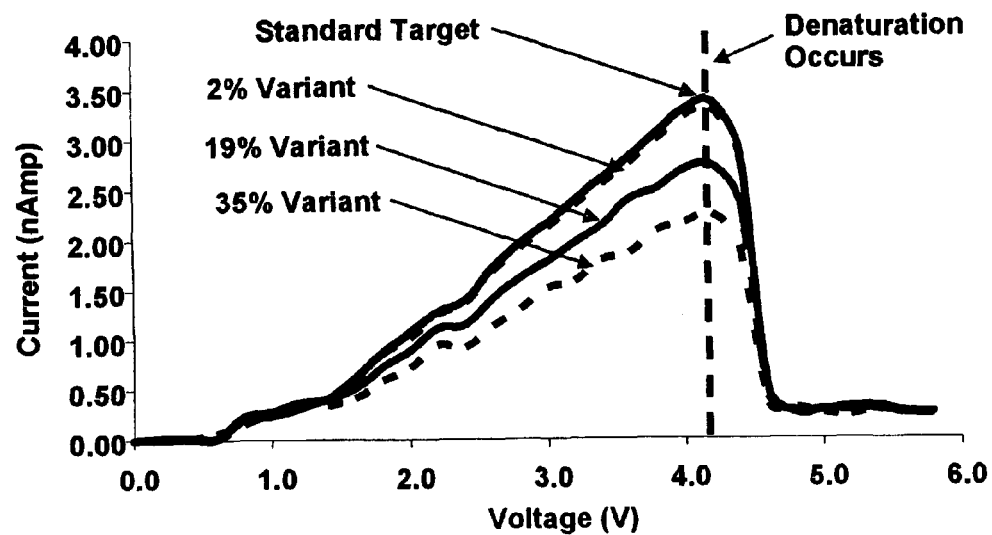
FIG. 6 illustrates a graph of current as a function of voltage.

FIG. 6 illustrates an example of current required to induce denaturation of tethered DNA from a complementary strand. The reset circuit, or other means of providing a denaturation current can remove the complementary strand from a sensor site, thereby readying it for a new sensing event. In one example, a sensor disposed in a flow stream can be used for successive and separate sensing events, thus, enabling continuous operation of the sensor.

In the figure, denatration current is indicated on the ordinate and applied voltage appears on the abscissa. The difference in current magnitude, as illustrated, provides a means for discerning variations from a complementary target molecule.

A high degree of proportionality is noted between the amount of current required to force denaturation and the degree of mismatch of the template and target ssDNA strands regardless of whether the variation occurred on one region of the genetic sequence or was spread out over a number of different locations along the sequence of the target.

FIGS. 7A and 7B illustrate a manual process of increasing the voltage to force denaturation followed by a reduction in the voltage back to sensing levels to allow another hybridization to occur. As illustrated in FIG. 7A, a number of sensing events are noted. Reset signals are illustrated in FIG. 7B, as corresponding to those sensing events. A denaturation current provides a means of resetting the sensor. The denaturation current appears consistent, both during the ssDNA and after hybridization (dsDNA) states.

In the figure, a complementary strand was introduced at approximately 15 seconds from the start of the data acquisition followed by an immediate sensing event. After several seconds, the voltage was manually increased to approximately 4 volts, resulting in denaturation of the double stranded DNA. The voltage was manually reduced to 3 volts, and the system was thus reset for another sensing event.

RESONANCE EXAMPLE

FIG. 8 includes graphical data 800 illustrating how resonance can be used to identify and detect a target molecule using a bridged template molecule.

In the figure, frequency is plotted on the abscissa and amplitude on the ordinate. The cantilever structure, or other suspended structure is driven to oscillate using an excitation signal. In various examples, the excitation signal is provided by a magnetic, piezoelectric or acoustical member disposed near the movable structure.

In the figure, curve 805 illustrates an example wherein the template molecule resonates at an initial frequency of $F_2$ and with an initial amplitude of $A_2$. After exposing the template molecule to the target molecule, the structure resonates with a frequency of $F_1$ and with an amplitude of $A_1$. Frequency difference $\Delta_F$ and amplitude difference $\Delta_A$ are indicative of the degree of homology and therefore, allow detection and identification of the target molecule. For example, it is believed that a target molecule with a higher percentage of match with the template molecule will exhibit a greater change in either or both of the amplitude and the frequency.

The figure illustrates a reduction in both the amplitude and the frequency. However, in other examples, either or both of the amplitude and frequency may exhibit an increase or a decrease.

In one example, resonance of the mobile portion of the MEMS device allows detection and identification. In one example, an end of the cantilever includes a magnetic material and an alternating current passed through a coil disposed under the cantilever causes the cantilever to vibrate at the frequency of the alternating current. In one example, the dimensions of the cantilever and the alternating current are selected to maximize the output. For example, if the alternating current is near the natural frequency of the cantilever, the response of the structural system will be maximized. The stiffness of the structural system is changed when the ssDNA, or other template molecule, is tethered between the end of the cantilever and the substrate base. Either or both the amplitude of the displacement of the oscillating system and the oscillation frequency will differ from that of the system with the free cantilever end. Upon introduction of a target molecule (such as an analyte or the ssDNA complement to the template ssDNA), the amplitude of the displacement and frequency of the oscillating system will change. The amount of the change will be proportional to the degree of homology between the template and target molecules since the stiffness of a dsDNA strand is greater than the sum of the stiffnesses of two independent ssDNA. Thus, in addition to the detection of the presence of the analyte, the change in amplitude and frequency can be used to measure the degree of homology of the ssDNA molecules when compared to that of a complementary match.

Exemplary Preparation

Figure 9:
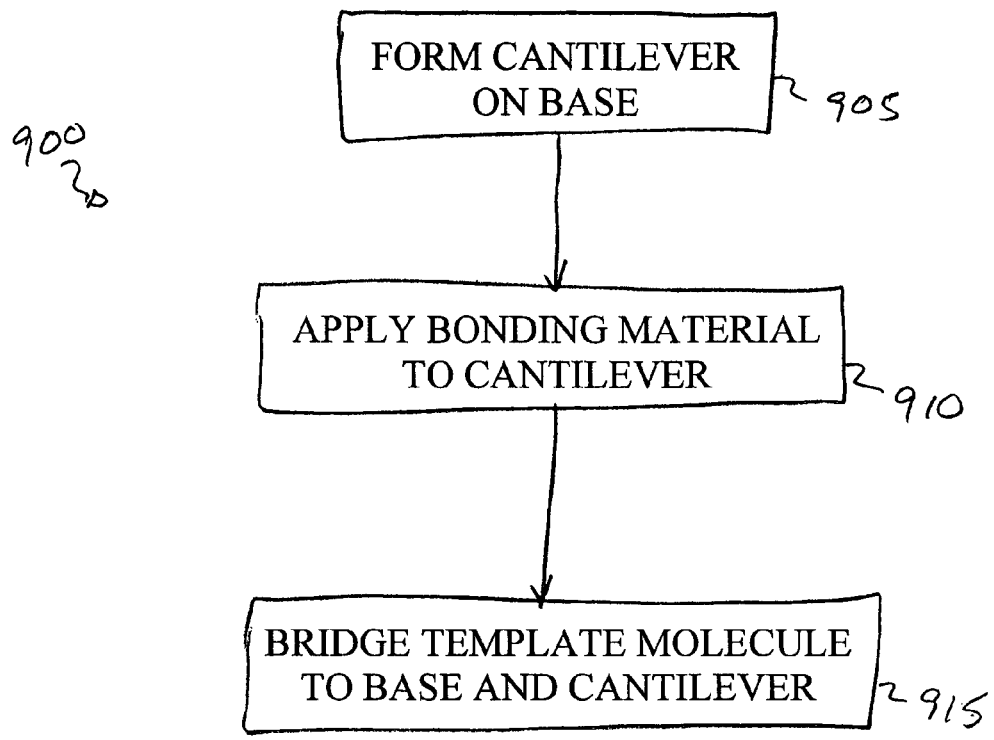
FIG. 9 illustrates a flow chart for a method of preparing a template molecule.

FIG. 9 illustrates a flow chart of method 900 according to one example. In the figure, a cantilever is formed on a base at 905. Structures other than a cantilever are also contemplated, including, for example, a circular or helical structure having one supported end and a free end. In addition, a disc-shaped or rectangular structure is also contemplated with a movable center region and a perimeter affixed to a base structure in the manner of a drum head. In one example, semiconductor fabrication techniques are used for the formation of the cantilever on the base.

At 910, a bonding material, or primer, is applied to the cantilever and to the base structure or substrate. The primer is selected to assure that the template molecule is affixed with proper alignment and orientation. In various examples, the primer includes gold and streptavidin.

At 915, the template molecule is bridged between the substrate and the cantilever.

In one example, method 900 is performed by a manufacturer in preparing a sensor for a particular application.

Exemplary Detection and Identification

Figure 10:
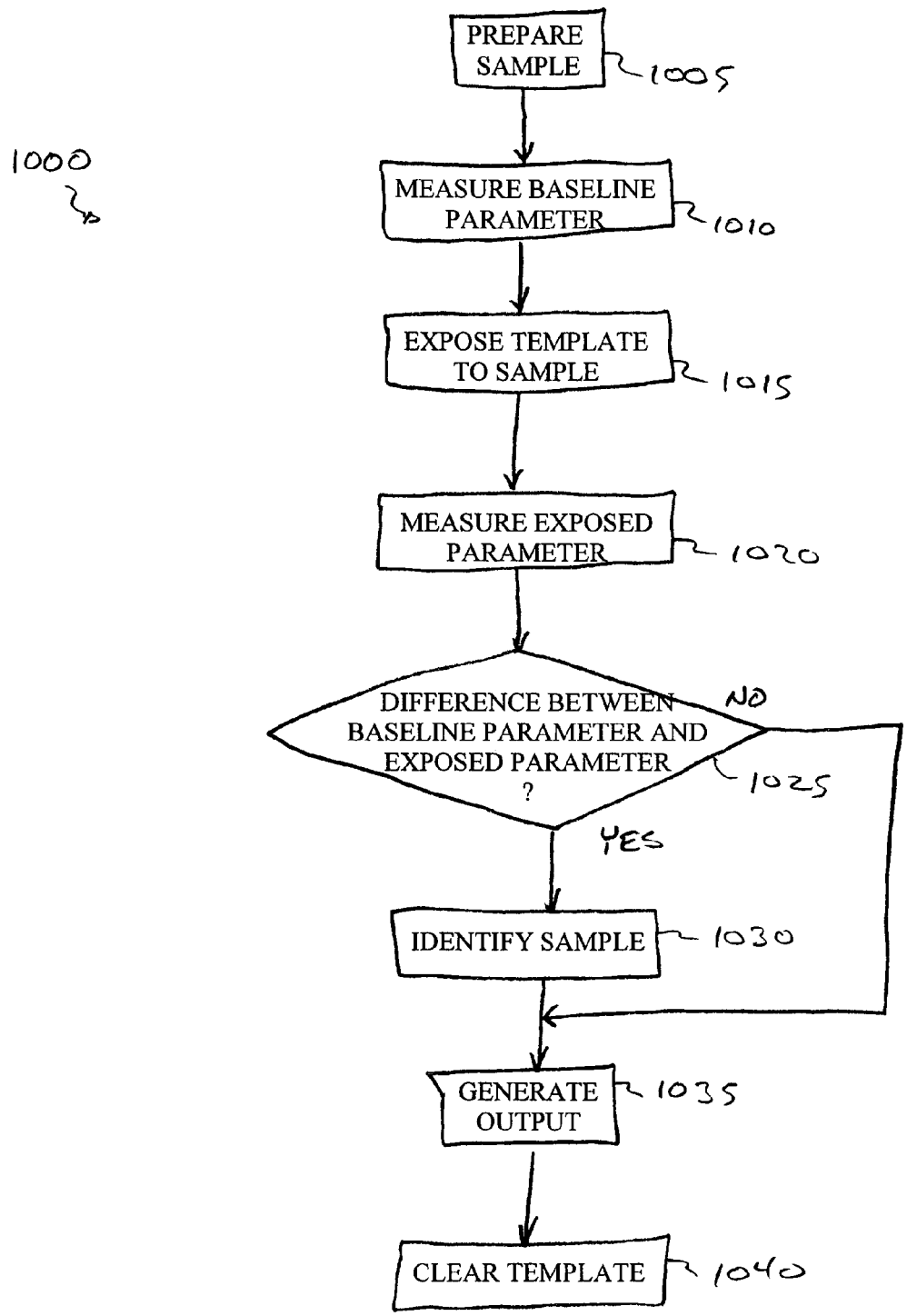
FIGS. 10 and 11 illustrate flow charts for methods of detecting a target molecule.
Figure 11:
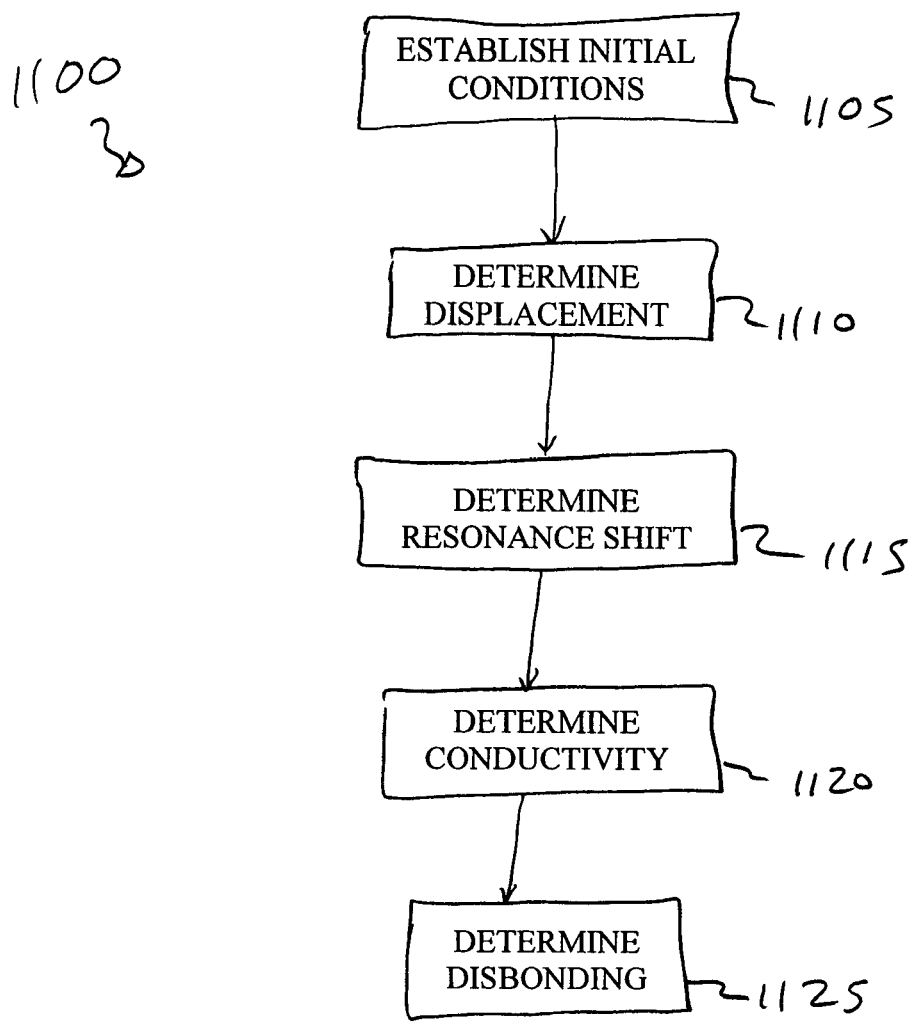

FIGS. 10 and 11 illustrate testing methods 1000 and method 1100, respectively. The methods illustrated, as well as other methods, can be implemented using a computer, or other control circuitry, coupled to a sensor. In one example, the method is executed using manual control of the sensor.

In FIG. 10, the sample is prepared at 1005. Sample preparation, in various examples, entails filtration, purification, amplification and other procedures to ready the sample for analysis.

At 1010, the template molecule is analyzed to establish one or more parameters to serve as a baseline. In one example, this entails verifying that the template molecule is properly aligned and positioned by verifying a current level through the template molecule. In addition, the conductivity or resistivity, resonant amplitude and frequency for the template molecule alone is measured. In one example, the physical position of the template molecule is measured.

At 1015, the sample is exposed to the template. In one example, this entails injecting a sample, which possibly includes the target molecule, into a channel or reservoir of the test apparatus. The channel or reservoir is in communication with the template molecule.

At 1020, the template molecule is analyzed to generate a physical parameter corresponding to the exposed template molecule. The exposed parameter, in various examples, includes measuring a change in a position, or displacement, measuring a change in alignment, measuring conductivity or resistance, measuring a denaturing current and measuring changes in resonance. Other physical parameters are also contemplated, including those based on a color or optical property of the combination of the template and target molecules.

At 1025, a query is presented to determine if a difference is noted between the baseline and the parameter after exposure of the sensor to the target molecule. If a change in the physical parameter, or a difference, is noted, then processing continues at 1030 where the sample is identified. The existence of a difference is indicative of detection of the template molecule.

As noted elsewhere in this document, the degree of homology is indicative of the match between the template molecule and the target molecule. Other binding pairs are also contemplated and proximity to a complete match can be correlated to the difference noted in the physical parameters.

In one example, a memory coupled to a processor of the present subject matter includes stored data in the form of a look-up table. The stored data provides a correlation between the differences or changes noted in a physical parameter and the degree of homology.

If the query at 1025 yields a negative answer, then processing continues to 1035 where an output signal is generated. The output signal, in various embodiments, includes a measure of the difference or change noted, the degree of homology or the identification of the target molecule.

At 1040, the template molecule is cleared of any remaining target molecule or sample material, or reset, by applying an electrical excitation to the template molecule and inducing denaturation or disbonding.

In one example, following 1040, the method returns to 1005 for detection and identification of an additional sample.

FIG. 11 illustrates method 1100 which includes a serial testing of a sample. It will be appreciated that other orders of testing are also contemplated as well as parallel testing. For example, measurement of a change in resonant frequency, resonant amplitude and conductivity can be performed concurrently. In method 1100, the initial conditions, or baseline, established at 1105.

At 1110, the displacement of the sensor, due to the template molecule hybridizing with the target molecule, is determined. At 1115, a shift in resonance is determined. The shift may correspond to a change in the resonant frequency or the resonant amplitude. At 1120, the conductivity of the template molecule with target molecule is determined. At 1125, a disbonding current, or heat level, is determined by monitoring for a peak signal.

Figure 12:
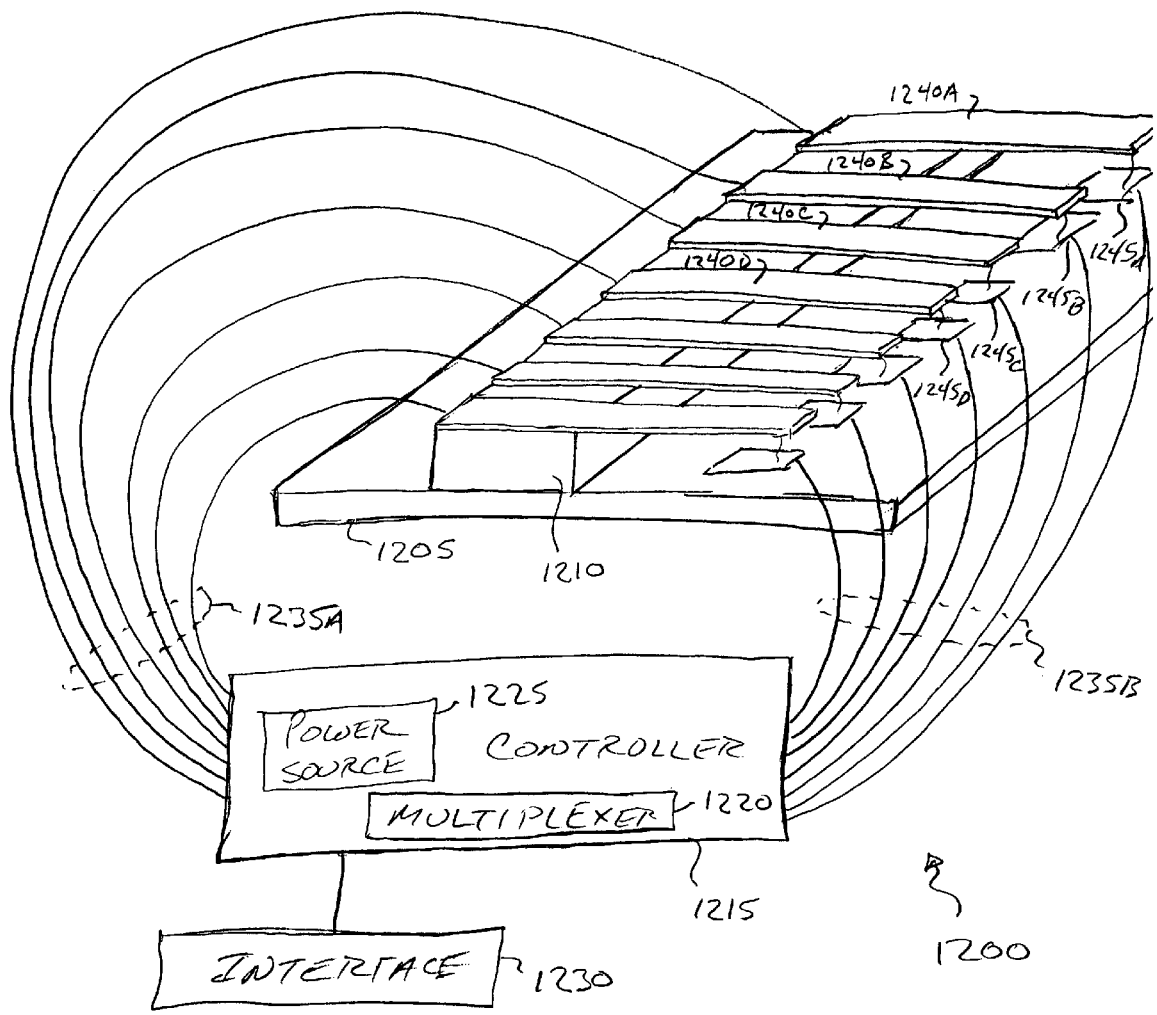
FIG. 12 schematically illustrates an array of cantilevers in a system.

FIG. 12 illustrates an array of cantilever sensors fabricated on substrate 1205 having common base 1210. The cantilevers, some of which are labeled 1240A, 1240B, 1240C and 1240D are affixed to base 1210 on one end and tethered by template molecules to contact points 1245A, 1245B, 1245C and 1245D, respectively, on a surface of substrate 1205. The template molecules, in one example, are of identical composition and provide a level of redundancy for testing. In one example, at least two template molecules are different and are tailored to detect and identify different target molecules.

Each cantilever, such as 1240A, is coupled to controller 1215 by electrical conductors 1235A and 1235B using multiplexer 1220. Controller 1215 selectively applies testing current, voltage, drive signals or other signals to enable each cantilever to detect and identify a target molecule. Power source 1225, of controller 1215 provides a constant or ramped voltage or current for excitation. In one example, power source 1225 provides a denaturing current or voltage. In one example, power source 1225 provides a drive signal to excite resonance in each cantilever.

Interface 1230 is coupled to controller 1215 and provides data entry and data output. In various examples, interface 1230 includes a display, a touch sensitive screen, a keyboard, a keypad, a mouse or other pointer control, an audio transducer, a storage device, a printer, a network connection (for example, a wide area network such as the Internet, or a local area network such as an intranet), an electrical connector or a wireless transceiver.

Figure 13:
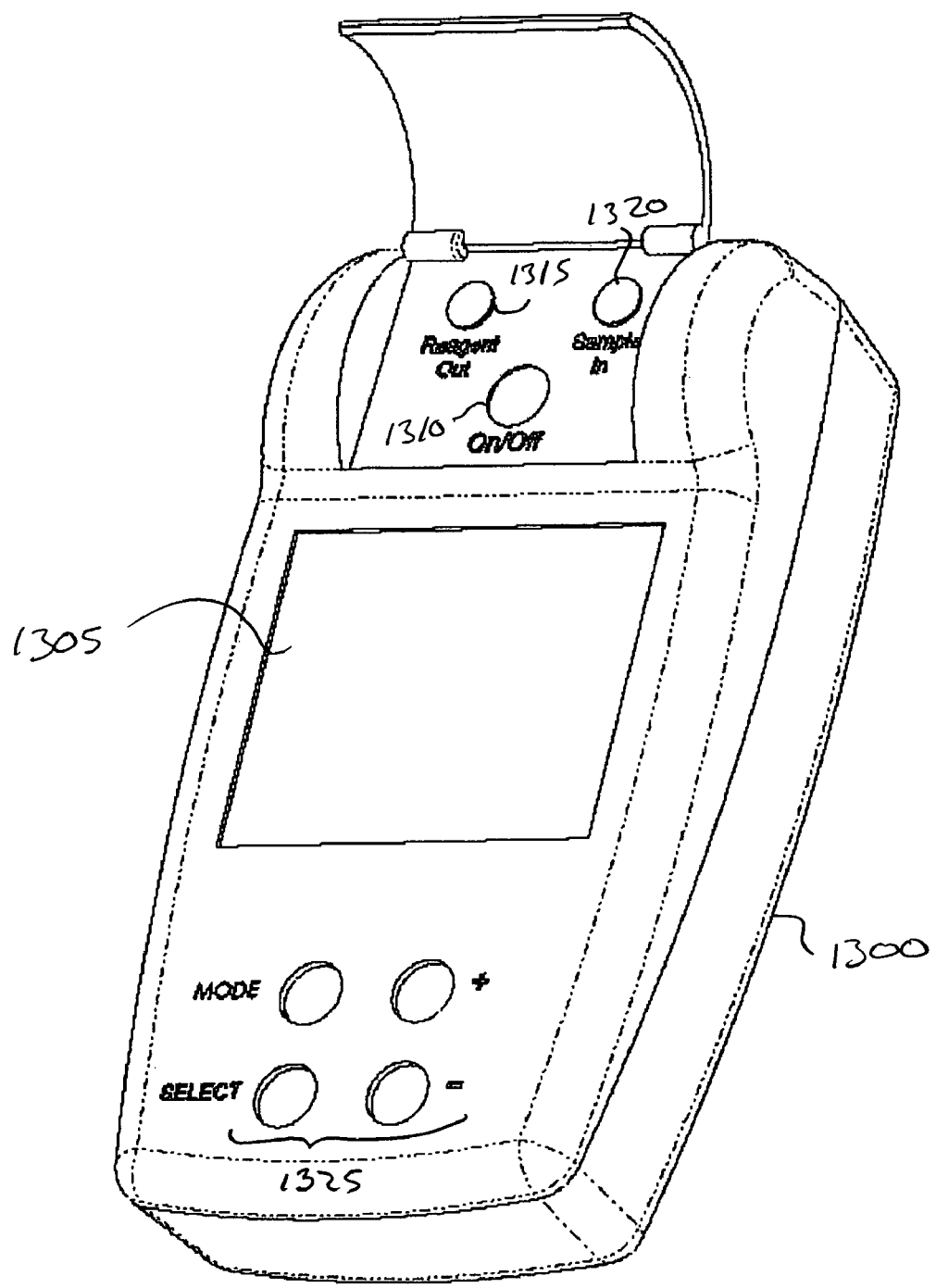
FIG. 13 illustrates an example of a portable detector.

FIG. 13 illustrates exemplary portable device 1300 according to one embodiment. In the figure, display 1305 provides visual prompts and data corresponding to analysis of a target molecule and device condition. User accessible controls and data entry points include power button 1310, reagent cut 1315, sample input 1320 and controls 1325. Other controls and data entry devices are also contemplated. In one example, a permeable surface on device 1300 allows a user to deliver a sample using a syringe or other injection device. In one example, a port on a surface of 1300 includes a reservoir to receive a sample.

Device 1300 is illustrated as a portable, battery operated device, however, other embodiments are also contemplated, including for example, a desk-top unit with accommodations for receiving a sample and providing an output.

EXAMPLE

In addition to measurable changes in length or force, the capacity of DNA structures to conduct an electrical current is related to content, sequence, length, and bridged circuit chemical environment. In one example, conductivity is related to levels of guanine/cytosine.

In one example, a 121 base pair (bp) *Bacillus* genomic DNA sequence was isolated from genomic, plasmid, and lambda viral DNA. Data indicates consistent results using numerous variables with regard to DNA properties (length, sequence composition) and analysis conditions (redox, pH, salt, denaturant, and hybridization accelerant controls) and other DNA (single and double stranded), molecules and genetic variants isolated from *Bacillus* as well as *E. coli* DNA.

The subject fragment was isolated from *Bacillus* genomic DNA by restriction endonuclease digest and ligated into a pUC 13 plasmid cloning vector that was transformed into an *E. coli* host as the parental strain. A library of random genetic point mutations were created along the length of the plasmid insert and isolates with inserts that varied from the parental by 2%, 19%, and 35% were sequenced and used for further analysis. Both parental and variant inserts were excised from the host plasmid and the 5' and 3' ends were chemically modified with a thiol and biotin groups. Single strand DNA was isolated using affinity chromatography (based upon the biotin modifications) and attached between streptavidin and gold coated conductive atomic force microscopy (AFM) tips and stages. The AFM tip is initially undeflected. In one example, the change in effective length of a single strand of DNA as it hybridizes to its complementary strand is a reduction of 40%.

AFM tip displacement was observed within seconds of introducing the DNA complement (in hybridization solution) or genetic variants to the tethered DNA template. The experimental results indicated a consistent tip displacement (<0.5% COV) as a function of the degree of mismatch between template and complement. It is postulated that base-pair mismatches did not contribute to overall structure helical formation, thus reducing the reduction of molecule length.

Electrical conductivity was determined utilizing conductive AFM tips. The same 121 bp fragment was tethered between AFM tip and stage and the DNA complement was introduced. Electrical current (in nanoamps) was measured as a function of time at a fixed voltage.

Prior to the introduction of the complementary DNA, the applied voltage resulted in a consistent, or baseline, current (of approximately 0.3 nA) passing through the tethered ssDNA. Treatment of the tethered ssDNA with DNA nuclease resulted in a loss of this baseline current. Heat treated nuclease did not result in a loss of current.

Measurable current through a sensor provides a verification of sensor function (sensor self-test) since electric current will flow if the ssDNA remains tethered to the MEMS mobile elements. Following hybridization between the tethered ssDNA and its complementary strand, an increase in current appears as noted in the figures. In addition, the figures illustrate a relationship between measured current and the degree of match between the strands. After hybridization, the conducted current remains relatively consistent as long as the voltage is applied to the sensor site.

After hybridization, the applied voltage was increased and the conducted current correspondingly increased to a peak level. Denaturation of the tethered ssDNA and the complementary strand occurred at a potential of approximately 4.1 volts for this particular 121 bp fragment. The amount of current associated with denaturation varied with the degree of match between the tethered ssDNA and the complementary strand. Concurrent with the drop in current, the AFM tip returned to an undeflected position. It is postulated that the higher level of current infuses sufficient energy into the hybridized strands such that they can no longer remain hybridized although other mechanisms or factors may be responsible for this phenomena. The base pair mismatches present in the variants appear to introduce insulating locations along the strands, thereby proportionately reducing conductance.

In one example, the selection of a template molecule, such as particular DNA, to bridge a circuit or cantilever structure affects DNA specificity, length, sequence, composition and conductivity. In one example, detection and identification specificity is enhanced by selecting ssDNA from multiple genetic regions of a pathogen for tethering. In one example, a longer DNA segment provides increased specificity (DNA sequence that is unique to the specific biological agent target). In one example, a shorter DNA segment allows selection of regions of high guanine (G) and cytosine (C) content. GC overall composition and sequence provides insulating characteristics of adenine (A) and thymine (T). High AT content in DNA leads to inflexibility and overall molecular curvature depending upon the relative positioning of AT-rich regions (i.e. in phase with the helical rotation). In various embodiments, selected DNA segments were greater than 40% GC, or greater than 60% GC. DNA segment length was therefore less than 500 base-pair (bp), or less than 150-200 base pair (bp). Determination of DNA GC composition, sequence, and specificity was determined using commercially and publicly available software such as PubMed BLAST (see the URL at ncbi.nlm.nih.gov/). Other software is available to correlate first order molecular parameters to higher order features (i.e. flexibility, curvature). In one example, the template molecule is selected using a software algorithm.

ADDITIONAL EXAMPLES

In one example, the sensor includes a suspended member which includes a cantilever. The template molecule is affixed to a contact point, at least one of which is located on the suspended member. The cantilever, in various examples, is curved, circular or web shaped. In one example, the suspended member is a rotary member that turns about an axis. As a rotary member, the contact point is displaced along an arc when the template molecule binds to the target molecule. In one example, one end of the rotary member rotates while another remains stationary or rotates in an opposite direction or through a smaller range and the phase difference between the two ends of the rotary member provides a difference signal that is used to discern the target molecule.

In one example, the template molecule has more than one binding site specific to a target molecule. In one example, the target molecule has multiple binding sites, each of which is specific to a different target molecule. In one example, the target molecule has multiple binding sites, each of which is specific to a single target molecule.

In one example, multiple contact points are provided on a sensor and the template molecule binds to two or more of multiple contact points. For example, a double-ended template molecule can bind to a sensor having two, three or more contact points. As another example, a three-ended template molecule can bind to a sensor having two, three, four or more contact points.

In one example, an output signal is generated as a function of a change in a measure of a physical parameter. Physical parameters include structural as well as electrical parameters. Exemplary structural parameters include positional changes such as physical displacement, resonant frequency, resonant amplitude, physical alignment or orientation of a contact point and a reference point, a force exerted on an axis, heat generated and optical changes including color. Other physical parameters are also contemplated.

In one example, an output signal is generated as a function of a change in a measure of an electrical parameter. Exemplary electrical parameters include impedance, conductivity, resistivity, inductance, capacitance. In addition, an electrical parameter can be described as an output signal in the presence of an input signal. For example, a change in current conducted in a template molecule can result in a change in voltage. In addition, a change in voltage applied to the template molecule can result in a change in a current. Other driving signals can also be applied and measured responses can be used to generate an output signal. Other electrical parameters are also contemplated.

In one example, a physical parameter includes a measurement of electrical conductivity. Electrical conductivity is a measure of the flow of electrons in a material. Electrical conductivity is the reciprocal of resistivity, or resistance, and in one example, the monitored physical parameter includes resistivity.

In one example, a ssDNA template molecule, bound via oligonucleotides primers, bridges an electronic MEMS based circuit. Hybridization to a target molecule (such as DNA) is derived from the microorganism being identified and causes a reduction in the distance between the cantilever elements.

In various embodiments, a comparator or Wheatstone bridge is used to detect, identify and compare voltage levels, current levels, conductivity or other parameters.

In one example, denaturing of the template molecule is performed by applying heat to the template and target molecules. A level of heat is quantified by measuring a current, voltage or wattage. In one example, a difference in the level of heat is correlated to the identity of the target molecule.

In one example, a single sensor site includes a tethered, single strand DNA (ssDNA) bridging a mobile element on a micro electromechanical system (MEMS) chip. In one example, hundreds or thousands of such sites are placed on a single chip. The tethered ssDNA is selected to hybridize with a complementary strand extracted from a bioagent of interest. The resulting hybridization both changes the physical length of the tethered molecule, and changes the conductivity of the tethered molecule. The changes are measured in a MEMS system at a high signal-to-noise ratio. The degree of change is related to the degree of match between the tethered and bioagent DNA strands. Thus, the degree of variance (specificity) of the bioagent can be measured. After detection, identification and discrimination are confirmed, the bioagent DNA strand is expelled from the tethered strand by increasing the current flow through the molecule, thus resetting the sensor for subsequent sensing events. Sensor viability is verified through a self-test since a tethered ssDNA (absent its complement) is able to conduct a measurable amount of current.

The physical parameter changes are proportional to the fidelity of match between the template molecule and the target molecule (or DNA strands) A single nucleotide mismatch yields a measurable change, thus enabling identification of various pathogens and differentiation of subtle variations between specific strains.

In one example, the template molecule includes ssDNA. In one example, specific DNA regions of *B. anthracis* are propagated and functionalized. The sensor can be bridged by DNA from any biological agent (bacteria, virus, or fungi).

In one example, four (4) 150-200 base pair (bp) segments of *Bacillus anthracis* (Ames) are selected for use as DNA bridge templates. In one example, for the purpose of testing the systems ability to discriminate between strains, alternative sequences to one of the templates was designed. The variants differ from the parent molecule by random nucleotide substitutions to generate 2%, 10%, and 20% variants. Template molecule selection is based upon calculated specificity, conductivity parameters, and flexibility. Species and strain specific segments were chosen from 16S rRNA fingerprint and virulence genes.

In one example, the four selected 150-200 bp templates and variants were synthesized through commercially available DNA synthesis facilities. The 150-200 bp DNA templates and variants were synthesized in ~50 bp ssDNA fragments. Hybridization and ligation steps were used to create full length 150-200 bp templates. The templates were ligated into an appropriate plasmid cloning vector and a library of the DNA bridge templates were generated in preparation of large-scale plasmid production. Optionally, the selected 150-200 bp template candidates are excised by restriction endonuclease digests or PCR amplified and subcloned from *Bacillus anthracis* (Ames) DNA.

In one example, DNA bridge templates were covalently attached to AFM and MEMS surfaces via biotin-streptavidin and thiol-gold bonds. The plasmid borne templates were restriction endonuclease excised, and 5-prime/3-prime biotin/thiol end-labeled with commercially available kits. In one example, the templates were PCR amplified using biotin and thiol labeled primers.

In one example, DNA templates and variants were verified for sequence integrity through commercially available subcontracted DNA sequencing services. The specificity of the each of the molecules was verified through standard Southern screening against genomic DNA of *Bacillus anthracis* strains (i.e. Ames, Sterne, A2012, 1055, Vollum, Kruger) and anthrax simulants (i.e. *B. globigii, B. cereus, B. subtilis, B. thuringiensis*) purchased commercially from the American Type Culture Collection or acquired through a material transfer agreement or other collaborators.

In one example, atomic force microscopy (AFM) was used to measure specific physical properties (i.e. displacement and conductivity) of the *B. anthracis* and variant ssDNA fragments. AFM tips and stages were coated with gold and streptavidin and the thiol/Biotin end labeled DNA bridge templates were attached. AFM tip displacement and material electrical properties were measured prior to, during, and after hybridization with complementary and variant ssDNA molecules and used as input into MEMS device design. In one example, reagents to control hybridization (pH buffers, salts), denaturation, hydrolysis and nucleotide oxidation were selected.

In one example, MEMS fabrication techniques are used for the construction of the sensor chips. In one example, fabrication entails deposition of thin films of material onto a substrate, application of a patterned mask onto the material using photolithographic methods and selective etching of the film using the resulting developed mask. Deposition of the material onto the substrate (silicon wafers) is accomplished by chemical reaction-based approaches (chemical vapor deposition, epitaxy, electrodeposition, or thermal oxidation) or by physical reaction-based approaches (evaporation, sputtering or casting). Removal of materials is accomplished through etching techniques. Thus, the circuitry for the device, using the application of patterned photolithographic masks, is constructed using appropriate application of insulating and conducting material layers. The fabrication facility incorporates the chip into packaging which, in one example, includes a ceramic or plastic housing for the chip that includes the pinned interface for attachment to a printed circuit board (PCB).

In one example, upon fabrication of the MEMS chips, the DNA bridge templates are generated and tested. In one example, the MEMS mobile elements (cantilever end) includes thiol/gold and biotin/streptavidin covalent bonds. Single molecule attachment was accomplished by electrostatic attraction. In one example, the device applies a 5 volt electrical potential across the gap between the mobile MEMS elements where the tethered ssDNA is desired, in series with a 10 MΩ resistor. The ssDNA molecule is attracted to the resulting electrical field. When in close proximity, the biotin-streptavidin bonds on the substrate base is formed, and the gold-thiol bonds is formed on the free end of the cantilever. When one molecule attaches in this manner, the potential across the gap is reduced due to the resistance in series in the circuit. Thus, a single ssDNA molecule attaches at each site. Excess DNA that does not bridge across the MEMS circuits is removed by DNA exonuclease digests. The circuit is stored in DNA stabilizing buffers (i.e., 300 mM NaCl, 10 mM Na citrate and 5 mM EDTA).

In one example, current measurement in the nano-amp range is performed using integrated circuit amplifiers. A multiplexing integrated circuit (IC) amplifier and other electronics and processing are used to display the results of the sensing events. Analog signals taken from the MEMS chip are amplified and converted into digital signals.

In one example, a printed circuit board includes accommodations for the attachment of the MEMS chip and the IC chip. The board also includes a dedicated main processing chip used to perform calculations and control electrical operations on the PCB. The PCB contains electrical interfaces for the display and the battery, as well as the menu buttons. In one example, a program executed by the main processor uses the digital signals output from the IC to provide display. The user interface includes controls to display and to set parameters that determine the display characteristics, the threshold detection values, battery level, on/off and pathogen molecule purging control.

In one example, a plastic housing contains the printed circuit board (and attached bio- and IC-chips), sample flow paths, LCD display and control buttons. In one example, an interior walls of the housing contain ledges and slots to contain electronic components and preclude shifting inside the housing. In one example, the housing includes one or more flow paths for introduction and removal of the reagents and sample.

In one example, electrical conduction through the sensor sites is greater than 0.2 nA using AFM electronics. In one example, the integrated circuit provides analog signal amplification >10 mV peak-to-peak.

In one example, the sensor is configured to detect and identify prepared genomic DNA of *Bacillus anthracis* strains and anthrax simulants (i.e. *B. globigii, B. cereus, B. subtilis, B. thuringiensis*), chemical and/or mechanically (sonicated) disrupted inactivated whole cell and spores of the previously mentioned anthrax strains and simulants, DNA and whole cells/spores in the presence of common contaminants and interferants such as postal dust, soil components, other chemical mixes, and mixed consortia of microorganisms.

In one example, the system includes signal amplification, processing and display sufficient to detect and identify a target molecule. In one example, electronic controls include on/off, mode, display control, battery life, self-test and reset functions. In one example, the system includes one or more flow passages to deliver a prepared sample to the surface of a sensor configured to identify a single predetermined pathogen, simulants or DNA target variants in a disruption solution.

In one example, the sample is collected outside of the system using surface wipe or batch air collector.

The present system includes a method and apparatus for determining the presence, the identity or quantity of a target substance comprising biological or chemical analytes. In one example, an electronic circuit including at least one deflectable arm of a bio-electronic cantilever is surface treated to facilitate binding to a template polymer molecule that undergoes a measurable change in a physical parameter in response to environmental changes, such as the presence of a target molecule associated with a target substance to be detected. For example, a change in the physical configuration or dimensions of the template molecule is translated into a deflection of a cantilever arm. In one example, a change in the electrical characteristics across the template molecule is detected by hybridizing a single-stranded DNA bridge template to its complimentary strand. Such changes in physical properties or parameters are measured to provide information related to the presence and identity of a substance of interest. In one example, a number of such circuits bridged by similar template molecules are provided and information related to the concentration or quantity of the target substance can be obtained.

In one example, a microcircuit with geometry tailored for use within a biological agent detection device is provided for detecting the presence of target and related biological agents or substances.

As used herein, a template molecule may be any molecule that will bind, or is likely to respond, to the presence or bind to a biological agent or a component of a biological agent. Accordingly, a template molecule may comprise a naturally occurring or synthetically formed biological molecule that will, or is capable of, selectively responding to, or binding to, a target molecule associated with the target substance to be detected. In one example, the template molecule includes an antibody, protein, nucleic acid, carbohydrate, glycoprotein or a polymer. In one example, the specific template molecule selected for detecting the presence of a particular target molecule (or species or genus of target molecule) is selected such that the template molecule responds to, or binds only with the exact target molecule or a related target molecule. In one example, a differential electric current or physical displacement results from a biomolecule—biomolecule recognition between the template and target. Accordingly, the relationship between a template molecule and a target molecule may be that of complementary strands of nucleic acids, including ribonucleic acids (RNA) and deoxyribonucleic acids (DNA) and derivative molecules. Further examples of the relationship between the template molecule and the target molecule include nucleic acid—nucleic acid recognition, protein—protein recognition, protein—nucleic acid recognition, protein—carbohydrate recognition, nucleic acid—carbohydrate recognition, and carbohydrate—carbohydrate recognition.

In one example, a biodetection device containing the described circuit including a template molecule spanning a gap between two surfaces, is provided. In one example, the two surfaces are movable relative to one another. When the template molecule is exposed to, or bound to, a target molecule, the template molecule undergoes a dimensional change, altering the distance between the two surfaces. Accordingly, a biodetection device in accordance with such an embodiment of the present invention can signal the presence of a target or related biological agent or substance when a change in the distance between the two surfaces is detected.

In one example, the amount by which the distance between the surfaces is altered is indicative of the molecule exposed to, or bound to, the template molecule. For instance, a target molecule that is an exact match for the template molecule (i.e., an "exact target molecule") may result in shortening the distance between the points of the template molecule interconnected to the two surfaces by an amount that is greater than the shortening that occurs when the template molecule is bound to a molecule that is related to but not an exact match for the template molecule. Accordingly, by measuring the amount by which the distance between the two surfaces has changed, information related to the identity of the molecule bound to the template molecule is obtained.

In one example, a biodetection device containing the described circuit capable of measuring the conductivity across a template molecule is provided. In particular, a template molecule is interconnected to first and second electrodes, such that it spans the gap between the two electrodes. When the template molecule is bound to a target molecule, the conductivity between the electrodes is altered. Accordingly, by detecting a change in the conductivity between the electrodes, the presence of a target molecule or related molecule can be detected. Furthermore, the amount by which the conductivity between the electrodes changes is indicative of the molecule bound to the template molecule. For example, an exact target molecule will cause a greater change in the observed conductivity between the electrodes than will a target molecule bound to the template molecule that is related but not identical to the exact target molecule.

In accordance with an embodiment of the present invention, a detection device that can be reused, without requiring the replacement of components, is provided. In particular, by heating the template molecule, the target or related molecule can be unbound from the template molecule. In accordance with an embodiment of the present invention, heating of the template molecule is accomplished by passing a current across the template molecule (and the bound molecule). Furthermore, the process of unbinding the target molecule from the template molecule can be used to obtain information related to the identity of the target molecule. In particular, the current applied across the template molecule (and target molecule) may be steadily increased or increased in steps, until a sudden change in the conductivity is observed, which indicates that the target molecule has been dissociated from the template molecule. Because the current, and therefore heat, necessary to unbind the target molecule is related to how closely matched the target molecule is to the template molecule, the amount of current required to unbind the target molecule is an indication of the closeness of the match between the bound molecule and the target molecule. For example, an exact target molecule would be expected to require more energy to unbind it from the template molecule than would a molecule that is not identical to the target molecule.

In one example, a biological agent detection device containing the described circuit combining a number of detection mechanisms or techniques is provided. For example, a detection device may determine the presence of a target biological agent by detecting a dimensional change experienced by a template molecule, by detecting a change in the conductivity across a template molecule, or by determining the amount of current required to unbind a target molecule from the template molecule. Furthermore, information for identifying the target molecule may be provided using such mechanisms or techniques.

In accordance with an embodiment of the present invention, a method for detecting target substances or analytes by detecting a change in a physical dimension associated with a template molecule is provided. According to such a method, a template molecule that undergoes a change in physical dimension when bound to a target molecule is exposed to a suspected biological agent or target substance (i.e., a substance suspected of containing a target molecule). The suspected biological agent may be derived from a gaseous, liquid, or solid medium. If the exact target molecule or a related molecule binds to the template molecule, the resulting dimensional change in the template molecule is detected, and the change reported. In accordance with a further embodiment, the method includes measuring the amount by which the physical dimension of the template molecule has changed.

In one example, a method for detecting a target substance by sensing a change in the conductivity associated with the template molecule in the presence of the analyte is provided. A template molecule capable of selectively binding to an exact target molecule or related target molecule is exposed to a suspected biological agent. According to the method, the conductivity across the template molecule is monitored. Upon becoming bound to a target molecule, the resulting change in the conductivity across the template molecule is detected, and that change is reported. In one example, the change in conductivity is measured.

In one example, a method for detecting the presence of a suspected biological agent by determining the amount of energy required to unbind a target molecule from a template molecule is provided. An electrical current is passed across the template molecule—target molecule pair. Furthermore, the amplitude of the current may be increased, until a sudden change in the conductivity across the template molecule is observed, indicating that the target molecule has become unbound from the template molecule. Furthermore, the current at which the target molecule is unbound from the template molecule is used to characterize or identify the target molecule that was bound to the template molecule.

The present system relates to the detection and identification of biological analytes. According to the present invention, target biological molecules are detected by sensing a change in a template biological molecule. The change in the template biological molecule may include a change in a physical dimension of the template molecule, a change in the electrical conductivity observed across the template molecule, and/or the energy required to dissociate a target molecule from the template molecule. The magnitude of the change in a physical dimension, change in conductivity, or amount of energy required to dissociate a target molecule from a template molecule, may be measured to determine the degree of homology between the target molecule and the template molecule. In a further aspect, the present invention provides a detection method and apparatus that does not require the replacement of components in order to make multiple readings.

In one example, an electronic circuit is bridged by a template molecule including a biological component or a representation of the biological component. In one example, the circuit includes a MEMS-based structure bridged by a nucleic acid molecule, such as a DNA molecule, or a molecule that physically and chemically represents a single strand DNA molecule. In one example, the MEMS circuit senses and responds to the motion and conductivity of a bridged DNA molecule as it hybridizes with its complimentary, or near complimentary DNA strand.

The following describes the selection and design of biological components of the bio-electronic circuit.

As used herein, biological detection and identification device specificity refers to the ability of the system to specifically and accurately identify a particular genus, species and strain of target biological agent. In the case, of DNA-based biological detectors/identifiers, the term specificity sometimes refers to the ability of the DNA components of the system to specifically compliment and hybridize to DNA isolated from the biological agent. In order to enhance detection and identification specificity, here, multiple (in one example, more than three), biological agent DNA segments are selected. The DNA segment selection is based upon the calculated length, specificity, conductivity parameters and flexibility of the molecule to bridge the MEMS circuit. Longer DNA segments tend to retain greater specificity (DNA sequence that is unique to the specific biological agent target), and yet shorter DNA segments allow selection of regions of high guanine (G) and cytosine (C) content. GC overall composition and sequence is related to the insulating characteristics of adenine (A) and thymine (T). In addition, high AT content in DNA leads to inflexibility and overall molecular curvature, depending upon the relative positioning of AT-rich regions (i.e. in phase with the helical rotation). Thus, selected DNA segments may be greater than 40% GC, or greater than 60% GC. In one example, DNA segment length is less than 500 base-pair (bp), or less than 150-200 base pair (bp). Determination of DNA GC composition, sequence, flexibility, curvature, and specificity is determined through a number of privately, commercially, and publicly available software such as PubMed BLAST (see the URL at ncbi.nlm.nih.gov/). In one example, four DNA template segments are 100% homologous to *Bacillus anthracis* (Ames) and show lesser homology to other *Bacillus* species and strains. Species and strain specific segments have been chosen from 16S rRNA fingerprint and virulence genes. In this embodiment, microorganisms outside of the. *Bacillus* genus fall below accurate detection and identification thresholds. In one example, a matrix includes DNA-bridged MEMS having DNA components that have specificity to other biological agents, and, in one example, is able to continuously monitor for the presence of agents simultaneously.

The following describes the production of the biological components of the bio-electronic circuit.

In one example, specific DNA regions of the targeted biological agent are selected, generated, mass produced and chemically modified for the sake of adherence to a MEMS circuit. In addition, variants of the DNA regions are also generated and produced for the purpose of testing the proposed circuit for discrimination capabilities. In one example, a variant is a DNA molecule that differs from the selected DNA template in nucleotide composition and sequence by 2% to 30%. In one example, four selected 150-200 bp segments are either synthesized, PCR amplified, or sub-cloned from an actual targeted biological agent. High fidelity DNA synthesis is generally limited to ~50 bp ssDNA fragments that then require hybridization and ligation steps in order to create the desired full length 150-200 bp DNA templates. The completed DNA templates are then attached directly to MEMS lead surfaces if the 5-prime and 3-prime ~50 bp synthesized fragments were specifically labeled with attachment ligands. Alternatively the completed 150-200 bp templates are ligated into a plasmid cloning vector and a library of the DNA bridge templates is generated in preparation for mass production. In one example, the selected DNA regions chosen to bridge the MEMS circuit leads may be excised by restriction endonuclease digests or PCR amplified, and sub-cloned from the targeted biological agent.

The following describes verification of biological component integrity.

In one example, DNA circuit bridge templates and variants are verified for sequence integrity. Sequence integrity refers to the actual nucleotide sequence as compared to the desired sequence. DNA sequencing methods will reveal the exact nucleotide sequence of the molecules intended to be labeled and attached to the MEMS lead surfaces. The present subject matter is sensitive to single base pair mismatches, thus, any sequence variation should be accounted for.

The following describes testing and analysis of biochemical and physical features of the biological component.

In one example, specific ssDNA molecules are selected, mass produced, and used to bridge the mobile elements of a MEMS circuit. The selection of the specific ssDNA molecules is based upon a number of biophysical features such as length, nucleotide composition and sequence, flexibility and mechanical motion, and conductivity parameters. The calculated motion and conductivity parameters are verified by atomic force microscopy (AFM) which can measure specific physical properties (i.e. molecular motion as determined by tip displacement and conductivity) of the ssDNA bridge template and variant ssDNA fragments. AFM tips and stages coated with gold and streptavidin according to published procedures are bridged by thiol/Biotin end labeled DNA bridge templates. AFM tip displacement and material electrical properties are measured prior to, during and subsequent to hybridization with complimentary and variant ssDNA molecules as input into MEMS device design.

Operational, chemical and temperature environments can be considered for specific ssDNA bridge templates. For example, reagents to control the effects of the user-defined operational environment, operational temperature, and DNA specific hybridization (pH buffers, salts), denaturation, hydrolysis and nucleotide oxidation can have an effect. In one example, operational reagents include:

a. Salts, pH, temperature
b. Hydrolysis control: Conductivity through aqueous environments may induce hydrolysis that could affect conductivity through the media. Control of this effect through the addition of appropriate reagents.
c. Oxidation control: Conductivity through DNA may induce oxidative damage particularly to the guanine residues. Control of this oxidative damage through the addition of antioxidants (i.e ascorbic acid, citric acid).
d. DNA thermal stability factors (i.e. 0.5-3 molar betains (N,N,N,-trimethylglycine; (Rees et al., Biochem., (1993) 32:137-144).
e. Denaturing reagents (i.e. 2-4 molar tetraethyl acetate, urea, chaotropic salts (i.e. trichloroacetate, perchlorate, thiocyanates and fluoroacetates), or glycerol, formamide, formaldehyde, and dimethylsulfoxide (DMSO).
f. Hybridization accelerants to enhance DNA to DNA hybridization through molecular exclusion phenomenon. Exemplary accelerants include mixtures of acetate salts and alcohols, certain amines (spermine, spermidine, polylysine) 0.1-0.5 molar detergents (dodecyl trimethylammonium bromide, and cetyltrimethylammonium bromide) and specific small proteins such as single stranded binding protein.

The following describes verification of DNA specificity.

In one example, DNA circuit bridge templates and variants are verified for sequence specificity. Software analysis of the selected DNA fragment may demonstrate the specificity of the fragment for one region of one strain of a targeted biological agent which may be confirmed through bioagent specificity screening.

An example of these methods includes Southern screening in which various restriction digested fragments of the bioagent target genome (and any other suspected related species) are electrophoretically resolved and transferred to a solid substrate (i.e. nylon or nitrocellulose). The fixed genomic DNA fragments may then be incubated with labeled (i.e. fluorescent or radioactive) DNA bridge template DNA. Under appropriate conditions (i.e. temperature, pH, and salt concentration) the template DNA will hybridize to a single fragment (assuming the genomic DNA restriction digests did not cut the fragment). Multiple sites of DNA template hybridization to the genomic DNA may entail modification of conditions in the biodetection device or selection of a new template DNA.

The following describes DNA bridge template end labeling.

In one example, synthesized, PCR amplified, or cloned DNA fragments (selected to bridge MEMS circuit leads) are attached to MEMS surfaces by any of the various methods concerning DNA attachment to organic or inorganic surfaces. In one example, orientation-specific immobilization is achieved when unique chemical moieties on the DNA bridge template termini and MEMS lead surface are cross linked. Commercially available chemical moiety-specific crosslinkers are generally based on nucleophilic substitution chemistry. This chemistry generally involves a direct displacement of a leaving group by an attacking nucleophile. In one example, the MEMS circuit leads include leads coated with gold and streptavidin respectively. In one embodiment, ssDNA bridge templates are covalently attached to AFM and MEMS surfaces via biotin-streptavidin and thiol-gold bonds. The DNA fragments are 5-prime/3-prime biotin/thiol end-labeled with commercially available kits or by any other means of labeling or functionalizing the 5' and 3' ends of DNA. Attachment chemistries can include, but is not limited to amino groups (such as N-hydroxy-succinimidyl esters), polyethylene glycols, carbodiimide, thiol groups (such as maleimide or a-haloacetyl), organo-silane groups, or biotin-streptavidin. In one example, DNA fragments are synthesized with 5' and 3' biotin or streptavidin modified nucleotides, or PCR amplified with biotin/streptavidin labeled primers from genomic or plasmid borne DNA targets.

The following describes an example of MEMS fabrication.

In one example, microelectromechanical systems (MEMS) refers to technology utilizing small mobile structures constructed on the millionth of a meter (micron) scale. These structures are made through the use of a number of tools and methodologies, similar to that used in the fabrication of integrated circuits (IC). MEMS devices, in one example, include combinations of mechanical elements and electrical elements, and, upon fabrication, are placed in a pinned packaging that allows attachment through a socket on a printed circuit board (PCB).

The following describes MEMS layered construction.

In general, fabrication of a MEMS device involves the deposition of thin films of material onto a substrate, the application of a patterned mask onto the material using photolithographic methods and the selective etching of the film using the resulting developed mask. Deposition of the material onto the substrate (usually silicon wafers) can be accomplished by chemical reaction-based approaches (chemical vapor deposition, epitaxy, electrodeposition, or thermal oxidation) or by physical reaction-based approaches (evaporation, sputtering or casting). Each of which varies in speed, accuracy and process cost; the applied material can be from a few nanometers to about 100 microns. Application of the pattern involves placing a photosensitive material on the surface, locating the patterned mask over the surface (typically with the aid of alignment marks on the surface and mask), and exposing the photosensitive material through the mask. Depending on the process used, either the positive or the negative of the exposed material can be removed, leaving the pattern on the substrate material. Other procedures includes preparing the surface, developing the photosensitive film and cleaning the result.

MEMS element manufacture may be performed using micro fabrication techniques. In one example, lithographic techniques are employed in fabrication using semi-conductor manufacturing procedures, such as photolithographic etching, plasma etching or wet chemical etching, on glass, quartz or silicon substrates.

The removal of materials is typically accomplished through wet etching, in which the material is dissolved away when immersed in a chemical solution, or dry etching, in which material is removed in a process essentially opposite physical reaction-based deposition. As with the various approaches to deposition, speed, accuracy and cost vary with the approach. In one example, etching of "deep" pockets from a substrate is performed with side wall aspect ratios at 50 to 1.

The MEMS device can be fabricated with one or more mobile elements, across which will be attached the template molecule of ssDNA. The mobile element, for example a cantilever beam, can be constructed so that both the beam and the substrate beneath the free end of the beam contain at least one conductive layer. Thus, the circuitry for the device, using patterned photolithographic masks, can be constructed using appropriate application of insulating and conducting material layers. In one example, the geometry allows for flow of sample from one DNA bridged MEMS to the next and re-circulating to enhance probability of contact and to conserve reagents. One embodiment includes an electronic circuit constructed on a support composed of such materials such as, but not limited to, glass, quartz, silicon, and various polymeric substrates, e.g. plastics.

In one example, various insulating layers are provided on the substrate. In one example, solid material amenable to supporting and responding to the described molecular properties (i.e. conductivity and motion) are used to construct the device. Although the figures in this disclosure may depict a flat positioning of the circuit, other embodiments include other orientation (i.e. vertical, etc.).

One example includes additional planar elements(s) which overlay the channels and reservoirs to enclose and seal to form conduits. This additional planar surface is attached by adhesives, thermal bonding, or natural adhesion in the presence of certain charged or hydrophilic substrates.

In one example, sample collection and preparation is completed outside the device. Samples are collected from surfaces using swabs or pads or collected in air or liquid by aspiration through filters, liquid traps or chromatography resins. Those samples are prepared by the addition of the reagents to disrupt the biological agent, release the target molecules and prepare those molecules for sensing by the device. The prepared sample are then be introduced into the device through a flow channel, reservoir or duct by syringe, pipette, eyedropper or other such manual or automated means.

One example includes air sample acquisition and preparation into the device itself for automatic operation through the presence of an on-board fan aspiration system. One example includes automated liquid sample collection and preparation into the device. Disruption of the samples can be provided by mechanical means, such as sonication techniques.

In one example, the sample is delivered through a flow path incorporated into the device to the surface of the biochip. The device includes reservoirs of reagents for sample preparation, as well as for system flushing, device calibration and waste material collection. In one example, the device includes means of pumping materials to and from these reservoirs. In one example, the device recirculates reagents through the system if no positive sensing event has occurred and the reagent remains of suitable purity.

In one example, oligonucleotide sequences are layered upon the leads to aide in the positioning and orientation of DNA bridge templates. In general, the oligonucleotide directed hybridization of DNA across a circuit is used to orient and position the single stranded DNA (ssDNA) bridge template. In one example, the ssDNA bridge template is bound to the MEMS leads via any method of attachment, including thiol or biotin mediated bonds.

Multiple DNA bridged MEMS circuits can be positioned on a single chip in a matrix or array geometry in order to enable simultaneous detection and identification of multiple pathogens from the same sample. In one example, the matrix includes multiple repeats of identical DNA bridged MEMS in order to enable concentration measurement of target DNA molecules as a function of the number of 'stimulated' circuits per volume of sample.

The following describes biological bridging of MEMS mobile elements.

After the physical MEMS device containing the mobile elements and the circuitry is fabricated, the single ssDNA molecule of interest (the template molecule) is attached to the device. In one example have a cantilever beam, the ssDNA is attached from the free end of the cantilever to the substrate base beneath the cantilever. In one example, the surfaces are prepared such that the functionalized ends of the template ssDNA will attach to the surface. The ssDNA is functionalized with a thiol group on one end (that has a high affinity for a gold surface) and biotin on the other end (that has a high affinity for a streptavidin-coated surface). Thus, if gold is used on the conductor on the bottom surface of the cantilever, the thiol-functionalized end of the ssDNA will attach to it. A gold surface on the substrate below the free end of the cantilever will also be exposed. Before introduction of the ssDNA template to be bound, biotin is electrostatically deposited on the gold surface on the substrate. Streptavidin is introduced over the wafer, which bonds to the biotinylated surface on the substrate. Accordingly, the surfaces of the MEMS device are prepared to bind the ssDNA template.

The following describes electrostatic trapping of a bridged molecule template which, in one example, includes attachment of a single ssDNA molecule across the gap between the free end of the cantilever and the prepared substrate base beneath it. In one example, an electrical potential is applied across the gap, in series with a large resistor. The ssDNA molecule is attracted to the resulting electrical field. When in close proximity, the biotin-streptavidin bonds on the substrate base are formed, and the gold-thiol bonds are formed on the free end of the cantilever. As soon as one molecule attaches in this manner, the potential across the gap is vastly reduced due to the resistance in series in the circuit. Thus, only one ssDNA molecule will attach at each site. Field assisted attraction of ssDNA to MEMS lead arms-device to aide in single molecule attachment. Electrostatic trapping of single conducting nanoparticles between nanoelectrodes. Appl. Phys. Lett. 71(9).

The following describes removal of excess template molecules.

In some cases, even though only one strand has attached across the gap, a number of ssDNA may be tethered to either the gold or the biotinilated surface. These "strays" have the potential of undesirably binding target pathogen ssDNA sequences. In one example, the device is treated with an exonuclease, to remove all ssDNA not tethered at both ends, thus eliminating the potential of binding events at other than sensor sites.

In one example, the system incorporates additional mobile elements, bridged with either synthetic or biological molecules, that act as reference or baseline controls for the elimination of mechanical, electrical or chemical background effects such as temperature, pressure, motion, stray voltage, induced electrical fields, and/or sample chemical contaminants. In one example, a device includes thousands of sensor and reference sites on one MEMS chip. The sensor sites may all include biological elements to detect the presence of a single bioagent, or may include a variety of biological elements to enable simultaneous detection of numerous bioagents on a single biochip.

The following describes integration of the MEMS circuit into signal amplification, processing, and display systems. Measuring current in the nano-amp range entails integrated circuit amplifiers. In one example, multiplexing and integrated circuit (IC) amplifiers and other electronics and processing are used to display the results of the sensing events. An integrated circuit is used to amplify analog signals from the MEMS chip and convert them into digital signals. In one example, IC fabrication incorporate the IC into packaging that allows pinned attachment of the IC to a printed circuit board (PCB). In addition to providing attachment of the MEMS and IC chips, the PCB includes a main processor to perform calculations and control electrical operations on the PCB. The PCB includes an electrical interface for the display and the battery, as well input/output to the menu buttons. In one example, the processor is programmed to use the digital signals output from the IC to provide display. The user interface includes direct controls of the display, and controls to set parameters that determine the display characteristics, the threshold detection values, battery level, on/off and bioagent molecule purging control. In one example, the PCB, display, user interface, battery and input/output are integrated into a plastic or metal housing.

The following describes testing and analysis of an exemplary system. One example entails sample collection, processing, and delivery to the electronic circuitry.

a. Sample Collection: The procedure for air, liquid, or solid sample collection are based on the target molecule source and instrument working environment. For example, particles of appropriate size, mass, or charge may be isolated and collected by filtration and/or mass spectrometry methods. Chemical or biological agents trapped on filters can be eluted by sample preparation reagents and delivered to the instrument. In one example, instrument aspiration technology is employed to draw or force air samples through sample preparation reagents that subsequently are delivered to the detection chip.

b. Sample Preparation: In one example, air, liquid, or solid samples are prepared externally to the detection device or internally via automatic sample preparation technologies. Specific steps and reagents for sample preparation depend upon the source and target molecules to be detected and identified. Chemical, thermal, and/or mechanical means are used to rupture biological cell contents and release target molecules. Similar means are used to prepare previously prepared organic or inorganic sources of target molecules. In general, disruption of biological cells requires detergents that solubilize lipid membranes, enzymatic digestion of proteins associated with cell membranes or target molecules, and various denaturants that modify or otherwise prepare the target molecules for detection and identification. Mechanical means include sonication or agitation, alone or in the presence of, disruptive beads. In one example, filtration or chromatography methods are used to purify the target molecules based upon size, hydrophilicity, charge, or ligand affinity. In one example, the system is resistant to target source associated components and other environmental contaminants (i.e. salts, dusts, solvents or reagents specifically added to inhibit proper detection or identification. In one example, the system is sensitive trace amounts of target molecule associated with the sample. In one example, the system detects and identifies specific DNA fragments found in, on the surface of, or other wise associated with the DNA source (i.e. microbe, animal cell, virus). In one example, the double stranded DNA is fragmented and denatured.

c. Sample delivery to microchip.
d. Detection, identification and discrimination occurs.
e. Result displayed on device.

Exemplary applications for the present system include real time detection, identification, discrimination, and concentration measurement of components derived from sources including, but not limited to animals, bacteria, viruses, fungi, plants, archaea, found in soil, water, or air. Exemplary components include, but are not limited to organic (i.e. composed of nucleic acids, amino acids, or carbohydrates, etc.) or inorganic (i.e. metals, inorganic phosphates, etc.) related to human, plant, or animal pathogens, components and sources of concern to food safety, components and sources of concern to medical diseases, genetic sequences associated with pre-disposition of diseases, pre-symptomatic diagnosis of diseases in plants and animals, laboratory diagnostic tool of listed components or sources, a laboratory tool to monitor gene expression of specific RNA and identification of specific animals or persons through polymorphism ID.

In addition to DNA-DNA interaction, other alternatives are contemplated, including:

Protein—Protein
1) Prion protein interaction with other Prions. Bovine spongiform encephalopathy (BSE, also known as mad cow disease), is a neurodegenerative disease in cattle and ingestion of infected meat products causes Creutzfeldt-Jakob Disease (CJD and vCJD) in humans. Variations of BSE have been identified in animal species and all have been classified as transmissible spongiform encephalopathies (TSEs). BSE in cattle, or CJD in humans, results when a neural protein called a prion changes shape from its normal form to a misfolded infectious form. The mis-folded infectious prions then induce other prion proteins to also mis-fold. The present system can detect physical conformation of a normal prion to the infectious form. In one example, a normal prion protein is attached via surface exposed cysteine or histidine residues to gold, nickel or platinum coated MEMS surfaces.
2) Antibody—Antigen interaction. In one example, the mobile elements of a MEMS circuit are bridged with a naturally produced or synthetic representation of the antigen binding site of an antibody that is specific to an antigen from a particular biological or inorganic agent. In one example, the amino acid molecule representing the antigen binding site is attached to the mobile MEMS surfaces via similar chemistry noted above for prions. Interaction of bio-agent antigens with bridged antigen binding sites induces a structural change in the bridged element thus creating a measurable signal.

Protein—Carbohydrate (Glycoprotein Formation)
1) interactions between extra cellular carbohydrate epitopes and receptor proteins can be detected and analyzed. Examples of such biological processes include viral and bacterial infections. One exemplary model is the Jack bean (*Canavalia ensiformis*) protein concanavalin A (con A) with mannose sugars (Acta Crystallogr.,Sect.D 50 pp. 847 (1994)). One example includes bridging the mobile elements of a MEMS circuit with Con A via histidine or cysteine residues. Glucose containing samples bind and alter the dimensional configuration of the Con A protein thus generating a signal to the system. The present system including such a circuit can detect the presence and concentration of glucose residues in the case of diabetes control.
2) The glycolipid globotriaosyl ceramide, expressed on kidney cell surfaces acts as the receptor to the Shiga-like toxin 1 (SLT1), a member of the two-component bacterial toxins, through binding interactions between the protein's pentameric 'B' binding subunit.

Carbohydrate—Carbohydrate

Cell to cell interactions and cell adhesion forces are sometimes associated with carbohydrate interactions with other carbohydrates or glycoproteins (J Cell Biol. 2004 May 24;165(4):529-37. 2004 May 17). Glycosphingolipid (GSL) co-interaction appears to play a role in mouse melanoma cell adhesion. One exemplary system includes the creation of glycoprotein structures with GSL binding sites for the purpose of monitoring cancer cell growth.

In one example, a chemical and biological detection/identification system entails sample collection, sample processing and delivery, sample analysis technology, and signal processing and output.

Strength of a DNA strand and length are dependent upon base composition, sequence, and environment. On average, the diameter of dsDNA is 20 Angstroms (Å), and the distance between adjacent nucleotides 3.4 Å or approximately 34 Å for one full helical rotation. The dsDNA helix demonstrates two grooves, the minor groove (~12 Angstroms) and major groove (~22 Angstroms). The distance between adjacent nucleotides of ssDNA however is approximately 5.84 angstroms.

Molecular Contraction

The first physical phenomenon is related to the helical shape assumed by double stranded DNA (dsDNA). A single strand of DNA (ssDNA) is generally a linear physical structure of a length equal to approximately 5.84 Angstroms per nucleotide base. (The individual building blocks (bases) comprising a DNA strand are guanine (G), adenine (A), thymine (T), and cytosine (C)). The alignment and bonding of one strand of DNA with its complimentary strand (a process referred to as hybridization), results in a helical-shaped dsDNA structure with a reduced distance between nucleotide bases of 3.4 Angstroms. Therefore whereas 50 bases of ssDNA is approximately 292 Angstroms, the same number of nucleotides of dsDNA is only 175 Angstroms (17.5 nm), or an expected average reduction in DNA length of approximately 40% (dependent upon base composition, sequence, and environment). This reduction in length is a consistent and physically measurable event.

Additionally, the amount of overall change in length of the molecule is related to the degree of match between the first (template) ssDNA and the second (compliment or target), attaching strand. Under appropriate conditions, less than perfectly matched DNA strands will also hybridize. However, there is a proportionately lesser effect on length reduction. Thus, if the change in length is measured, and the maximum change in length due to a perfect match is known, the degree of variation of the genetic sequence between a target ssDNA and an introduced ssDNA can be determined. Environmental conditions that demand exact matches include low salt conditions and high temperatures (20C A&T, 40C G&C). Conversely, hybridization between in-exact matched DNA strands (or genetic variants) is possible by raising the salt conditions and lowering the temperature. The interaction of one ssDNA molecule with another and the resulting changes in physical conformation is critical to the function of the invention. The overall strength of strand-to-strand and sub-unit link bonding is a result of the combined attractive forces between individual units. These attractive forces include hydrogen bonding, base stacking interactions, and hydrophobic interactions that force bases into the interior and phosphates to the exterior. It is also important to realize that the exact measure of bonding energy is dependent upon neighboring nucleotides and nature of the environment (pH, temperature, ionic strength, etc.). Hydrogen bonding adds 4-7 kcal/mole, base stacking adds 3.8-14.6 kcal/mole, and the covalent bond energies of phosphodiester linkages (80-100 kcal/mole) (refereences). Experimental and theoretical studies confirm that the average base composition and sequence dsDNA tensile strength is approximately 5×10-12 Newtons (kg/sec2) (refereences). This force corresponds roughly to the weight of a single bacterium; nevertheless the techniques just mentioned are delicate enough to apply such forces accurately.

Conductivity

A second physiological phenomenon related to the recombination of two matching ssDNA is that there occurs a marked increase in conductivity of the ssDNA subsequent to hybridization. A number of research studies have proven that ssDNA is capable of conducting electricity. The conductivity of the ssDNA is highly dependent on the makeup of the genetic sequence, with guanine and cytosine (G and C) tending to act as conductors while adenine and thymine (A and T) tending to act more as insulators (refereences).

The increase in conductivity subsequent to hybridization can be as much as 100× that of ssDNA for appropriately G-C rich sequences. Debate exists in the literature as to the mechanism that allows this remarkable increase, be it electron tunneling through the base pair region or electron hopping in the sugar phosphate backbone; regardless of the mechanism, the increase is measurable and well above any signal-to-noise concerns.

As with the change in molecule length, the increase in conductivity is proportional to the degree of match between a target ssDNA and a potential matching ssDNA. The greater the mismatch between the ssDNA molecules, the less the increase in conductivity subsequent to hybridization.

Voltage Induced Denaturation

A third physiological phenomenon is related to the separation of a dsDNA into the two complimentary ssDNAs. Southern hybridization is a well-proven laboratory approach to control the hybridization and denaturation of DNA molecules (refereences). By controlling the environmental variables such as salinity and temperature, one can force hybridization or denaturation of the DNA molecules. Denaturation can also be effected by the passing of sufficient current through the dsDNA. Again, the ultimate mechanism is not completely understood; however, the phenomenon has been repeatedly observed (refereences). As with the changes in molecular length and conductivity, the current required to force denaturation of the dsDNA into the two component ssDNA is proportional to the degree of match between the component ssDNAs. The greater the match, the greater the current required to result in denaturation.

DNA Template Production

*Bacillus subtilis* Genomic DNA preparation: *Bacillus subtilis* (Ehrenberg) Cohn strain 168, (American Type Culture Collection (ATCC) #27370) was cultured in 100 ml sterilized ATCC media #265 composed of 12.5 g heart infusion broth (BD #238400), 5.4 g nutrient broth (BD #234000), and 2.5 g yeast extract (BD #212730) per liter. The cultures were grown for 15 hours at 30° C. with shaking at 140 rpm. Genomic DNA was purified from the cultures according to an adaptation of a standard procedure (Marmur, J. 1961. *A procedure for the isolation of deoxyribonucleic acid from microorganisms*. J. Mol. Biol. 3:208-218). Briefly, 100 ml *bacillus* cultures were centrifuged at 4000×g for 10 minutes. Pellets were resuspended and incubated for 1 hour at 37° C. in 9.5 ml TE (10 mM Tris (tris hydroxyl-aminomethane EM #9210), 1 mM EDTA (ethylene diamide tetra-acetic acid EM #4010)); 0.5 ml 10% SDS (sodium dodecyl sulfate EM#DX2490-2); and 50 microliters 20 mg/ml proteinase K (EM #24568-3). After incubation, 1.8 ml of 5M NaCl (sodium chloride VWR #6430-1) is added and the solution mixed thoroughly followed by the addition of 1.5 ml CTAB/NaCl solution (10% CTAB (hexadecyltrimethyl ammonium bromide VWR 80501-950) in 0.7 M NaCl)) and incubated at 65° C. for 20 minutes. The solution is extracted with an equal volume of chloroform (EM #CX1054-6)/isoamyl alcohol (Calbiochem #80055-544) and spun for 10 minutes at 6000×g at 22° C. The aqueous phase was extracted with phenol (EM #PXO511-1)/chloroform/isoamyl and spun for 10 minutes at 6000×g at 22° C. DNA in the aqueous phase was precipitated by the addition of 0.6 volumes of isopropyl alcohol (VWR 3424-7) and spun for 10 minutes at 6000×g at 4° C. The precipitate was washed with 70% (v/v) ethanol and resuspended in 4 ml TE. The concentration was determined by spectrophotometer absorbance at 260nm, and adjusted to 100 µg/ml. 200 µl of ethidium bromide (EM #4310) and 4.3 g of CsCl (cesium chloride EM #3030) were added per 4 ml of DNA. The solution was spun for 4 hours at 300,000×g at 15° C. The genomic DNA band was visualized by UV light and removed by syringe needle. The ethidium bromide was extracted with CsCl-saturated isopropanol, and the CsCl removed by overnight dialysis in 2 liters TE at 4° C. The DNA was precipitated with 0.6 volumes isopropyl alcohol and stored at −70° C.

PCR amplification of *Bacillus subtilis* 16S rRNA: The 16S rRNA gene of *B. subtilis* was PCR amplified from the genomic DNA prepared above according to published methods (H.-J. Bach,l, D. Errampalli, K. T., Leung, H., Lee, A,. Hartmann, J., T. Trevors, and J. C. Munch. 1999. *Specific Detection of the Gene for the Extracellular Neutral Protease of Bacillus cereus by PCR and Blot Hybridization*. Applied and Environmental Microbiology, p. 3226-3228, Vol. 65, No. 7). Amplification of DNA was carried out with the GeneAmp PCR System 9600 (Perkin-Elmer, Norwalk, Conn.). 50 µl samples contained 50 ng of template *B. subtilis* genomic DNA, 25 picomole of each primer (Forward: 5'-gggtttgatc-ctggctcag-3' (SEQ ID NO:1); Reverse: 5'-acggttaccttgttac-gactt-3' (SEQ ID NO:2)), 0.2 mM deoxynucleotide triphosphates (Boehringer, Mannheim, Germany), 2 units of Taq/AmpliTaq® DNA polymerase (Promega), 5 µl of 10× reaction buffer (EM), and 3 mM MgC12 (EM). The PCR program was as follows: hot start cycle of 94° C. for 5 min and 80° C. for 4 min; one cycle of 94° C. for 2 min, 64° C. for 1 min, and 72° C. for 2 min; 30 cycles of 94° C. for 30 seconds, 64° C. for 30 seconds, and 72° C. for 45 seconds; and a final extension at 72° C. for 10 minutes. Amplified PCR products were resolved by gel electrophoresis with 0.8% agarose (Promega LMP #V2831) in TAE buffer (40 mM Tris-acetate [pH 7.6], 1 mM Na$_2$EDTA). The approximately 1500 by PCR product was excised, and extracted from the agarose using AgarACE® (Promega) digestion method. (Note: the primers notes above have been specifically designed by Dr. Albert as tools to PCR amplify the 16S rRNA nucleotide sequence from numerous bacteria).

Cloning of Bacillus subtilis 16S rRNA: The 16S rRNA PCR product produced in the step above was ligated into plasmid cloning vector pGem®-T Easy (Promega) according to manufacturer's recommended procedure. Briefly, 75 ng PCR product was added to 5 µl 2× rapid ligation buffer (Promega), 1 µl (50 ng) vector DNA, and 1 µl (3 Weiss units) T4 DNA ligase. The reaction solution was incubated at 22° C. for one hour. The ligation reaction product was transformed into JM109 competent cells (Promega) according to the following procedure: 2 µl of ice cold ligation reaction was gently added to 50 µl of ice cold competent cells in a sterile 1.5 ml tube. The tube was incubated on ice for 20 minutes, followed by 50 seconds at 42° C., and returned to ice for 2 minutes. 950 µl of 22° C. sterile SOC medium was added and the tubes incubated at 37° C. for 1.5 hours shaking at 150 rpm. The transformed cells were plated on LB/ampicillin/IPTG/X-Gal plates. And the plates incubated at 37° C. for 20 hours. White colonies were subsequently screened for inserts by the plasmid miniprep procedure outlined below.

Plasmid miniprep procedure: Plasmids containing inserts of B. subtilis 16S rRNA nucleotide sequence were quickly purified from the JM109 E. coli hosts by a modification of the technique of Blin & Doly in Nucleic Acids Research 7:1513-1523 (1979). Twenty white colonies, representing candidate insert/vector transformed clones, were each picked by sterile pipette tip into 2 ml LB/ampicillin broth in a sterile capped test tube and incubated for 16 hours at 37° C. shaking at 200 rpm. The cultures were each added to a sterile 1.5 ml microcentrifuge tube and centrifuged at 4000×g for 5 minutes at 4° C. The pellets were resuspended in 180 µl Solution I plus 20 µl 5 mg/ml lysozyme and incubated at 22° C. for 5 minutes. 400 µl of solution II was added by inversion×5 and the solution was incubated on ice for 5 min. 300 µl ice cold solution III was added and the tube contents vortexed and incubated on ice for 10 minutes. The samples were centrifuged at 10,000×g for 2 minutes at 22° C., and the supernatant transferred to a new sterile 1.5 ml microcentrifuge tube containing 500 µl (0.6 volumes) of isopropanol to precipitate the DNA. The samples were vortexed and centrifuged at 10,000×g for 5 minutes at 22° C. and the pellets were resuspended in 200 µl of TE.

Screening transformants for 16S rRNA gene inserts: 5 µl of the plasmid preparation were restriction digested with Not I (Promega) according to manufactures direction, and plasmid and excised insert fragments were resolved by 1% agarose electrophoresis to identify colony isolates containing the desired pgem-B.subtils rRNA plasmid constructs. Clone candidates identified by electrophoretic analysis as harboring the appropriate plasmid construct were cultured in 500 ml LB/ampicillin media, aliquots were stored in 70% glycerol at −70° C., and large scale plasmid preps were conducted to establish a stock of cultures and DNA.

Alternative approaches toward generating the same 121 bp bridge template: Two alternatives toward generating the identical 121 bp nucleotide sequence are provided below.

1) Subcloning from B. subtilis DNA. Frequently, cloned fragments of microbial DNA can be obtained from personal or commercial sources. Plasmids containing large inserts of B. subtilis DNA that include the desired 121 bp fragment could be digested with the restriction enzymes Aat II and Sph I. The digest would release a 171 bp fragment that could be cloned into any appropriate cloning vector such as the pGem-T (Promega) Aat II/Sph I sites. The desired 121 bp fragment could be subcloned from this plasmid according to the PCR procedure indicated above.

2) Synthesis of the desired bridge templates. The desired oligonucleotide bridge templates may be synthesized on any commercially available system such as an ABI 392 DNA synthesizer. Standard phosphoramidite chemistry would be utilized resulting in a dimethoxy trityl protecting group on the 5' end. The molecules would be purified by C18 reverse phase HPLC (25 mM NH 4 OAc, pH 7, 5-25% CH 3 CN over 30 min) followed by deprotection in 80% acetic acid for 15 min. Following deprotection, the oligonucleotides would be purified a second time on the same C 18 column by reversed-phase HPLC (25 mM NH 4 OAc, pH 7, 2-20% CH 3 CN over 30 min). Synthesized DNA quantities would be determined UV-visible absorption spectroscopy using the following extinction coefficients for single-stranded DNA: (260 nm, M−1 cm−1) adenine (A)=15,000; guanine (G)=12,300; cytosine (C)=7400; thymine (T)=6700. Since most synthesis procedures loose fidelity beyond 70-90 bases, the 121 bp bridge template discussed here would be synthesized in at least two fragments. Specifically, as shown in step 1 of the research plan, four ~60 base single stranded nucleotides would be synthesized, and hybridized and ligated to each other in the appropriate manner. The product would then be ligated into a cloning vector.

Preparation of 121 bp circuit bridge template by PCR amplification: The 121 bp segment of the B. subtilis 16S rRNA gene was PCR amplified from the pGem-B.subtilis rRNA plasmid construct. 50 µl samples contained 50 ng of Sal I digested template plasmid DNA, 25 picomole of each primer (Forward: 5'-CGAGCGGCCGCCTGGGCTACA-CACGTGC-3' (SEQ ID NO:3); Reverse: 5'-CGACCGCG-GCCAGCTTCACGCAGTCG-3' (SEQ ID NO:4)), 0.2 mM deoxynucleotide triphosphates (Boehringer, Mannheim, Germany), 2 units of Taq/AmpliTaq® DNA polymerase (Promega), 5 µl of 10× reaction buffer (EM), and 3 mM MgCl$_2$ (EM). The PCR program was as follows: hot start cycle of 94° C. for 5 min and 80° C. for 4 min; one cycle of 94° C. for 2 min, 64° C. for 1 min, and 72° C. for 2 min; 30 cycles of 94° C. for 30 seconds, 64° C. for 30 seconds, and 72° C. for 45 seconds; and a final extension at 72° C. for 10 minutes. Amplified PCR products were resolved by gel electrophoresis with 1.5% agarose (Promega LMP #V2831) in TAE buffer (40 mM Tris-acetate [pH 7.6], 1 mM Na$_2$EDTA). The approximately 121 bp PCR product was excised, extracted from the agarose using AgarACE® (Promega) digestion method. The purified product was ligated to the Not I/Sac II site of pGem vector, transformed in JM109, and 121 bp insert containing plasmid was produced as described above.

DNA Bridge Template Specificity Verification: The 121 bp B. subtilis fragment cloned by the procedure described above was verified for sequence integrity through commercially available subcontracted DNA sequencing services. It was determined that the 121 bp insert nucleotide sequence was: 5'-ctgggctacacacgtgctacaatggaca-gaacaaagggcagcgaaaccgcgaggttaagccaat Cccacaaatctgttct-cagttcggatcgcagtctgcaactcgactgcgtgaagctgg-3', and is an exact match to 16S rRNA Bacillus subtilis subspecies subtilis strain 168 (Entrez PubMed accession #NC000964).

The specificity of the 121 bp insert was verified through standard Southern screening against genomic DNA of *Bacillus subtilis* and other *Bacillus* species (i.e. *B. globigii, B. cereus, B. subtilis, B. thuringiensis*) purchased commercially from the American Type Culture Collection. Southern hybridization screening involved the following procedure. *Bacillus* species genomic DNA, generated as described above, was restriction digested with restriction enzymes Hind III, EcoR I, and Pst I which do not digest the 121 bp insert. The fragments generated by the digests were resolved on 0.8% agarose in TAE and stained with ethidium bromide. The gel was UV treated at 260 nm for 5 minutes on a transilluminator, subsequently soaked in 0.2 M HCl for 7 minutes. The gel was then soaked in base solution (1.5M NaCl, 0.5M NaOH) for 45 minutes, followed by the neutralizing solution (5 M Tris-HCl, 3M NaCl, pH 7.4) for 90 minutes. In standard Southern configuration (Southern, E.M. (1975) Detection of specific sequences among DNA fragments separated by gel electrophoresis. J. Mol. Biol.98, 503-517). Briefly the treated gel is sandwiched between absorbent Whatman 3MM filter paper and a DNA binding nitrocellulose (SS), such that 20×SSPE (3 M NaCl, 0.2 M NaH2PO4, 20 mM EDTA, pH 7.0) is wicked through filter paper, and through the gel as it transfers the gel DNA onto the binding membrane. The genomic DNA was allowed to transfer for 16 hours at room temperature. The membrane was removed and soaked in 5×SSPE for 30 minutes and baked in an 80° C. vacuum oven a few hours until the filter was dry. The membrane was then probed for fragments that would hybridize to the above 121 bp cloned template fragment labeled according to manufactures direction Alk-Phos®-DIRECT(Pharmacia). Color development of the probed membrane clearly indicated that the probe was specific to *B. subtilis*, and to only a single site within the *B. subtilis* genome.

Generation of point mutant variants: Genetic variants of the 121 bp nucleotide sequence were created by published methods (Molecular Biology: Current Innovations and Future Trends. Eds. A. M. Griffin and H. G. Griffin. ISBN 1-898486-01-8. 1995 Horizon Scientific Press, PO Box 1, Wymondham, Norfolk, U.K). Specifically, 0.5 pmole pGem-*B.subtilis* plasmid template DNA was added to a PCR cocktail containing, in 25 ul of 1× mutagenesis buffer: (20 mM Tris HCl, pH 7.5; 8 mM MgCl2; 40 ug/ml BSA); 20 pmole each of T7 and SP6 primers (Promega), 250 uM each dNTP, 2.5 U Taq DNA polymerase, 2.5 U of Taq Extender (Stratagene). The PCR cycling parameters were 1 cycle of: 4 min at 94° C., 2 min at 50° C. and 2 min at 72° C.; followed by 5-10 cycles of 1 min at 94° C., 2 min at 54° C. and 1 min at 72° C. The parental template DNA and the linear, mutagenesis-primer incorporating newly synthesized DNA were treated with DpnI (10 U) and Pfu DNA polymerase (2.5U). This resulted in the DpnI digestion of the in vivo methylated parental template and hybrid DNA. Pfu DNA polymerase removed the Taq DNA polymerase-extended base(s) on the linear PCR product. The reaction was incubated at 37° C. for 30 min and then transferred to 72° C. for an additional 30 min. 115 ul mutagenesis buffer containing 0.5 mM ATP was added and the solution mixed. 4 units T4 DNA ligase was added to 10 ul of the solution in a new microfuge tube and incubated for 90 min at 37° C. The solution is transformed into competent JM109 *E. coli* as indicated above and plated on LB/ampicillin for 16 hours at 37° C. Plasmid DNA was generated from individual isolates and the nucleotide sequence determined as indicated above. Isolates demonstrating 2%, 19%, and 35% base mutation were saved for further study.

End labeling of 121 bp templates: DNA bridge templates will be covalently attached to AFM and MEMS surfaces via biotin-streptavidin and thiol-gold bonds. The plasmid containing the 121 bp 16S rRNA *B. subtilis* fragment was restriction digested with Not I and Sac II to release the insert which was gel purified on 0.8% LMP agarose in TAE buffer as described above. The 5'-ends and 3'-ends of the molecules were respectively labeled with thiol and biotin chemistry using commercially available (Pierce #89818) end-labeling kits and according to published procedures (B. A. Connolly and P. Rider, Nucleic Acids Res. 13, 4485 (1985). AND A. Kumar, S. Dvani, H. Dawar, G. P. Talwar, ibid. 19, 4561 (1991).

Measurement of DNA Physical Properties: Atomic force microscopy (AFM) is typically used to assess the topography of a surface at the molecular level. The AFM system includes a cantilever arm with a sharp tip protruding orthogonal to the longitudinal axis of the arm. The arm is lowered until the tip comes into contact with the surface, and then is pulled along the surface measuring changes in surface dimensions. The movement of the cantilever tip is measured; the process is repeated over enough of the sample surface to characterize the topography. Most commonly, the tip deflection is measured using a reflected laser approach.

In this work, AFM was used for sake of either measuring the force required to break the bonds along the axis of a single or double stranded DNA molecule, to measure the displacement of the AFM tip as a result of the motion of bound DNA molecules.

Experimental measurements of resistance to force applied to a molecule tethered between an AFM tip and stage: A molecule loosely tethered between tip and stage is initially compressed in standard AFM fashion until a positive force is recorded. As the tip is subsequently lifted from the surface, the molecule becomes taut resulting in a negative force recording until the distance between tip and stage exceeds maximum molecular length at which point the molecule breaks.

Atomic force microscopy (AFM) was used to accurately measure specific physical properties (i.e. displacement and conductivity) of the *B. subtilis* 121 bp insert and variant DNA fragments. The AFM was operated according to prescribed chemistry and methodology. AFM tips and stages were coated with gold and streptavidin according to published procedures, and the thiol/Biotin end labeled DNA bridge templates generated above were attached (R M Zimmermann and E C Cox. 1994. *DNA stretching on functionalized gold surfaces*. Nucleic Acids Research, Vol 22, Issue 3 492-497). Prior to attachment, the end-labeled DNA thiol group was deprotected overnight with 0.04 M DTT, 0.17 M phosphate buffer, pH 8.0. Repeated extractions with ethyl acetate to remove excess DTT was performed just prior to attachment in 10 mM HEPES, 5 mM EDTA buffer, pH 6.6. Gold treated AFM tips were submerged in the DNA solution for 2 hours at room temperature and dried under a nitrogen stream. The DNA-bound AFM tips were mounted in the AFM, and the reaction chamber flooded with SPE (0.1 M sodium phosphate pH 6.6, 1 mM EDTA, and 1M sodium chloride) to allow for the formation of covalent biotin-streptavidin bonds.

AFM tip displacement and material electrical properties were measured prior to, during, and subsequent to hybridization with complementary and variant ssDNA molecules. Reagents that controlled hybridization (pH buffers, salts), denaturation, hydrolysis and nucleotide oxidation were examined.

Experiment concerning tip displacement from fixed state: The length of a single strand of tethered DNA is reduced as a result of hybridization with its complimentary strand. Under these experimental conditions, the length reduction of the tethered ssDNA results in a measurable displacement of the AFM tip toward the stage.

Results

This work described here actually encompassed molecular and AFM research on approximately 80 molecules ranging in size from 83 bp to 2854 bp in length. The DNA was derived from plasmid vectors, lambda virus, *E. coli* genome, and *B. subtilis* genome DNA. Although the most intensive studies were conducted on the 121 bp fragment described above, the results were similar across all molecules. Initial studies measured the reduction of length of the single strand of 121 bp fragment attached at both ends to the AFM tip and stage according to methods discussed earlier. AFM tip displacement was observed within seconds of pipetting 4-5 µl of dilute (1-2 molecules per µl) single stranded 121 bp fragments, or denatured plasmid containing the 121 bp insert. FIG. 4 shows how the 121 bp fragment reduced in length by approximately 10 nm.

The exact length of a strand of DNA is dependent upon base composition, sequence, and environment. On average, the diameter of dsDNA is 20 Angstroms (Å), and the distance between adjacent nucleotides is 3.4 Å or approximately 34 Å for one full helical rotation. The dsDNA helix demonstrates two grooves; the minor groove (~12 Angstroms) and major groove (~22 Angstroms). The distance between adjacent nucleotides of ssDNA however is approximately 5.84 angstroms. Therefore whereas 121 bases of ssDNA is approximately 701 Angstroms, the same number of nucleotides of dsDNA should be approximately 411 Angstroms, or an expected average reduction in DNA length of approximately 40%. Therefore, if the 121 bp strand tethered in the AFM were allowed to twist freely, the tip should have been displaced by as much as 29 nm.

The separate introduction of DNA molecules that differed from the parental nucleotide sequence by 2%, 19%, and 35% (variants) demonstrated a measurable difference in tip displacement. If AFM tip displacement in these studies was due to double strand DNA helical formation with a length less than that of the single strand DNA, then it would follow that hybrid molecules composed of less complementary strands would demonstrate less tip displacement.

FIG. 4 illustrates the 121 bp DNA bridge template was tethered, and held at slight tension between AFM tip and stage as discussed in the text, for a time prior to approximately 15 seconds. The tip, held at a steady state position of approximately 71 nm moved approximately 10 nm upon introduction of the template's complementary DNA strand. Separate introduction of molecules that varied from the parental by 2%, 19%, and 35% resulted in a measurable difference in tip displacement. Graph lines depict less than 0.3% deviation over 5 measurements each.

AFM cantilever surfaces were gold coated to allow the conductance of electrical current through molecules of study. By applying a potential between the cantilever and the stage, a corresponding current was measured through the bridged 121 bp ssDNA template. For an applied voltage of approximately one volt, the current measured through the ssDNA template was approximately 0.3 nA. When a perfectly complimentary target ssDNA was introduced the measured current at the same voltage rose to approximately 2.1 nA.

These results confirm the behavior related to ssDNA/dsDNA conductivity discussed earlier. The conductivity of the DNA molecule was also confirmed to be dependent on the composition and sequence of the DNA molecule. Specifically, adenine (A) and thymine (T) nucleotides act as insulators whereas guanine (G) and cytosine (C) nucleotides are better conductors.

Similar results occur when target ssDNA strands are introduced that are an engineered variant with a known degree of variation from the template. The same variant target ssDNA molecules used in the deformation studies were introduced, with the conductivity response measured accordingly. Of note is the high degree of proportionality between the conductivity increase of the molecules upon hybridization and the degree of mismatch of the template and target ssDNA strands, providing experimental proof of the specificity phenomenon outlined earlier. The results were consistent whether the variation occurred on one region of the genetic sequence, or was spread out over a number of different locations along the sequence of the target.

Once the amount of conducted current was measured through the dsDNA, the applied voltage was manually increased across the AFM cantilever and the substrate, resulting in increased conductance through the dsDNA. The voltage was increased until denaturation of the dsDNA occurred. A plot of results for such experiments are shown in FIG. 6. At the point of denaturation, the current conducted dropped back down to the level associated with ssDNA.

From FIG. 6, there was a high degree of proportionality between the amount of current required to force denaturation and the degree of mismatch of the template and target ssDNA strands. As with the prior studies, the results were consistent whether the variation occurred on one region of the genetic sequence or was spread out over a number of different locations along the sequence of the target.

Another experiment conducted with the AFM involved increasing the voltage to force denaturation, and then reducing the voltage back to sensing levels to allow another hybridization to occur. As can be seen in FIG. 7, the AFM successfully performed a number of sensing events, and validated the use of the current sensing of hybridization/forced denaturation by increased current as a means of resetting the biosensor. Of note in FIG. 7 is the consistency of the measured current, both during the ssDNA and after hybridization (dsDNA) states, throughout the multiple sensing events. While the experiment depicted in FIG. 7 shows four discrete sensing events, a number of the experiments were actually conducted through hundreds of sensing events, with no notable degradation of the signal and no significant change in the measured currents before and after sensing.

The AFM allows investigation and verification of the phenomena outlined in the prior section. The sensing events involved selected attributes of a dedicated biodetection device. For example, AFM cantilever tips are constructed using the same approach and techniques as used device manufacturing, the sensor device involving the AFM utilized one ssDNA as a sensing site.

Research plan to synthesize a 121 bp DNA bridge template:

Step 1. Synthesis of molecule fragments (A+, A−, B+, and B−) with linkers (small case)

```
(A+) = 5'-CTGGGCTACACACGTGCTACAATGGACAGAACAAAGGGCAGCGAAACCGCGAGGTTAAGCCAATCC
(SEQ ID NO: 6)

(B+) = 5'-CACAAATCTGTTCTCAGTTCGGATCGCAGTCTGCAACTCGACTGCGTGAAGCTGGgcatg
(SEQ ID NO: 7)

(A−) = 3'- tgcaGACCCGATGTGTGCACGATGTTACCTGTCTTGTTTCCCGTCGCTTTGGCGCT
(SEQ ID NO: 8)

(B−) = 3'- CCAATTCGGTTAGGGTGTTTAGACAAGAGTCAAGCCTAGCGTCAGACGTTGAGCTGACGCACTTCGACC
(SEQ ID NO: 9)
```

Step 2. Hybridization of molecule fragments (A+ to A−, and B+ to B−)
(A+/A−)—Heat to 95 Celsius, slow cool to room temperature

```
CTGGGCTACACACGTGCTACAATGGACAGAACAAAGGGCAGCGAAACCGCGAGGTTAAGCCAATCC
(SEQ ID NO: 6)

tgcaGACCCGATGTGTGCACGATGTTACCTGTCTTGTTTCCCGTCGCTTTGGCGCT
(SEQ ID NO: 8)
```

(B+/B−)—Heat to 95 Celsius, slow cool to room temperature

```
CACAAATCTGTTCTCAGTTCGGATCGCAGTCTGCAACTCGACTGCGTGAAGCTGGgcatg
(SEQ ID NO: 7)

CCAATTCGGTTAGGGTGTTTAGACAAGAGTCAAGCCTAGCGTCAGACGTTGAGCTGACGCACTTCGACC
(SEQ ID NO: 9)
```

Step 3. Ligate fragments A+/A− to B+/B−
(A+/A−)—In 1× ligation buffer plus T4 DNA ligase at room temperature

```
CTGGGCTACA----ACCGCGAGGTTAAGCCAATCCCACAAATCTGTT---GTGAAGCTGGgcatg
(SEQ ID NO: 10)

tgcaGACCCGATGT----TGGCGCTCCAATTCGGTTAGGGTGTTTAGACAA---CACTTCGACC
(SEQ ID NO: 11)
```

The resulting 121 bp molecules can then be ligated into the Aat II/Sph I cloning sites of pGem-T.

Solutions:
Solution I: 50 mM Glucose (0.9% w/v); 25 mM Tris pH 8, 10 mM EDTA pH 7.5
Solution II: 0.2 N NaOH, 1% SDS
Solution III: 2.7 M potassium acetate to pH 4.8 with glacial acetic acid.
SOC Medium=(per 100 ml: 2 grams Bactog-tryptone (BD), 0.5 grams yeast extract (BD), 1 ml 1 molar NaCl, 0.25 ml 1 molar KCl, 1 ml 2 molar $Mg^{+2}$ stock, 1 ml 2 molar glucose)
$Mg^{+2}$ stock=1 molar $MgCl_2$, 1 molar $MgS0_4$
LB/ampicillin/IPTG/X-Gal plates=per liter add 15 grams agar (BD), 10 grams Bacto®-tryptone (BD), 5 grams yeast extract (BD), and 5 grams NaCl; adjust pH with NaOH; autoclave, cool to 50° C.; add ampicillin to 100 micrograms per ml, IPTG to 0.5 milimolar, and 80 micrograms per milliliter X-Gal. Pour 30-35 ml of medium per 85 mm plate, let agar harden at 22° C., and store 4° C.

Abbreviations:
ml:millileter, μl:microliter, g:gram, mg:milligram, ng:nanogram, M:molar (moles/liter), mM:millimolar, (BD=Becton, Dickinson and Company, Franklin Lakes, N.J.)

(EM=EMD Chemical Inc., Gibbstown, N.J.)
(VWR=VWR International, West Chester, Pa.)
(Calbiochem/Novabiochm Corp, San Diego, Calif.)

(Promega=Promega Corporation Madison, Wis.)
(Pierce=Pierce Biotechnology Inc., Rockford, Ill.)

All chemical and biological detection/identification systems must incorporate (A) sample collection, (B) sample processing and delivery, (C) sample analysis technology, and (D) signal processing and output (FIG. 1). In one example, the microchip, or series of microchips, is composed of thousands of DNA sensitive cantilevers called micro-electromechanical systems (MEMS) arranged in a manner to allow for the detection, identification, and concentration flux of multiple pathogens (multiplex).

Each well on a microchip may contain a single or hundreds of cantilever-based circuits. Each circuit is composed of some form of mobile element bridged by preferably a biological molecule such that when the molecule interacts with other molecules, the associated motion causes the cantilevers to move. Numerous geometries are possible such as a single cantilever suspended over a stage as depicted in the AFM drawings, a single rotating disc or other shape, or two cantilever arms that move relative to each other as depicted in FIG. 10. A matrix of these bridged cantilevers, or wells of these cantilevers, could be constructed such that on one axis redundant identical circuits measure the concentration of a single biological agent depending on the number of circuits that respond to the presence of the bio-agent. Each row of these cantilevers, or wells of these cantilevers, could be dedicated to a different biological agent. Each chip would also contain a significant number of reference cantilevers to respond to background levels of chemical, mechanical, or other environmental 'noise'. A biodetection/identification device could include chips that are dedicated toward a particular array of biological agents. For example, one device may contain a chip with cantilevers bridged by molecules that would only react with agents associated with homeland security. Other devices may contain bridged cantilevers that only respond to food safety, or agents important to the medical or agricultural industries.

As the biological molecule responds to changes in its environment, the mobile elements will deflect, and that subsequent deflection is measured. The measurement of motion in MEMS devices is well documented. One way to measure the deformation is to reflect a laser beam off a surface on the deformable element. As the molecule responds, the element moves, and the laser beam is subsequently deflected to different receptor locations. The change in the reflected beam is measured by the different receptor locations and correlated to the amount of physical response exhibited by the molecule.

The present sensitivities are about 10 angstroms for displacement and 5 pico-Newtons for force, but improvements as the size of the device shrinks are expected. The smallest transistor-probe structure reported has dimensions of 3×2 microns×140 nm. Stanford's Thomas Kenny reported on the use of slender cantilevers in atomic force microscopes to measure forces at the attonewton (10-18 newton) level.

Several alternate methods for measuring the deformation of the mobile MEMS elements also exist. One method is to include a layer of piezoelectric material on the deformable elements themselves. Another involves adding a mass of magnetic material at the end of a mobile MEMS element and measuring the change in magnetic field as the mobile element is moved by the biological element's responses. Yet another involves measuring changes in the capacitance across the gap bridged by the biological element as it is moved by the biological element.

The mobile elements of the MEMS device shall also comprise a circuit, including the template molecule. Thus, a voltage can be applied across the mobile elements, and a resulting current will pass through the ssDNA. The increase in conductivity through the circuit subsequent to hybridization will be measured by sensing the increase in current flow, amplifying that signal and converting the result to digital output for processing.

During normal operation, when a sensor site is in its ready state (a detection event has not yet occurred), the voltage across the mobile elements will be set to a "sensing" level. This level is high enough to allow measurable current, but too low to be near the denaturation limit. This current seems to have the additional benefit of drawing target ssDNA to the sensing site, most likely through electrophoresis.

Passing a current through the ssDNA has an additional benefit. Since the ssDNA is capable of passing a small amount of current by itself (prior to hybridization), the device has an inherent self-test. If the ssDNA template is damaged, broken, or comes loose from the mobile MEMS elements, the circuit is no longer complete. Thus, the ability of each sensor site to be in a ready state for a sensing event is able to be validated. If a specific site is found to be inoperable, that signals from that site can be removed in software from inclusion in future calculations for pathogen presence and concentration calculations.

Having the circuit completed by the template ssDNA will also allow the ability to measure the third phenomenon noted earlier: effecting denaturation using electrical current. The applied voltage can be increased to a level that results in sufficient current to denature the dsDNA. This provides the sensor with the ability to reset itself, in that after a sensing event occurs, the pathogen attached to the template portion of the device can be repelled. The repelled ssDNA target is swept away in the material flowing through the sensor, the voltage is lowered back down to its sensing level, and the sensor site is then ready for another sensing event.

The size of these elements is extremely small, such that potentially thousands of sensor sites could be located on a MEMS chip the size of a penny. Thus, a number of virulence gene regions could be included on a given chip for a specific pathogen, and additionally, a number of pathogens could be included on a given chip as well.

In various examples, the sensor of the present subject matter is coupled to a detector. In one example, the detector includes an electrical circuit and is referred to as a detector circuit. In one example, the detector utilizes non-electrical means for discerning a physical displacement or resonance condition. In the absence of a modifier, the term detector includes both electrical and non-electrical detectors.

It is to be understood that the above description is intended to be illustrative, and not restrictive. For example, the above-described embodiments, or aspects thereof, may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

What is claimed is:

1. A device comprising:
a template molecule linked between at least two contact points including a first contact point disposed on a first surface and a second contact point disposed on a second surface, wherein the first surface is independent of the second surface, and wherein the template molecule includes at least one recognition site for a target molecule; and
a detector coupled to the first contact point and the second contact point, the first contact point and the second contact point having a first physical parameter, the detector configured to generate an output signal based on a change in the first physical parameter indicative of electrical conduction through the template molecule, wherein the change in the first physical parameter corresponds to an association between the target molecule and the template molecule, wherein a single stranded conductive nucleic acid molecule is selected as the template molecule; and
wherein the template molecule, the first contact point, the detector and the second contact point form an electrical circuit, and further, wherein the detector comprises a driving circuit for providing a current or voltage through the electrical circuit for disassociating the template molecule from the target molecule.

2. The device of claim 1 wherein the template molecule is ssDNA or ssRNA.

3. The device of claim 1 wherein the target molecule is a nucleic acid comprising a sequence sufficiently complementary to a sequence in the template molecule so that the target molecule will hybridize to said template molecule.

4. The device of claim 1 wherein the template molecule is a nucleic acid that is bonded to the first contact point at its 3'-end and to the second contact point at its 5'- end.

5. The device of claim 1 further comprising a second physical parameter which includes at least one of:
a resonant frequency of the first contact point relative to a reference point;
a resonant amplitude of the first contact point relative to the reference point;
a distance between the first contact point and the reference point; and
an alignment between the first contact point and the reference point.

6. The device of claim 5 wherein the reference point includes the second contact point.

7. The device of claim 1 wherein the first surface includes a movable surface.

8. The device of claim 1 wherein the detector includes at least one of an optical sensor, a magnetic field sensor, an electric field sensor, a capacitance sensor, a resistance sensor and a strain sensor.

9. The device of claim 1 wherein the detector includes at least one of a comparator and a bridge circuit.

10. The device of claim 1 wherein the detector includes a resonance driver in communication with the first surface.

11. The device of claim 5 wherein the detector is configured to generate the output signal based on a change in the second physical parameter.

12. The device of claim 1 wherein the detector is coupled to the second contact point and wherein the first contact point having a first physical parameter includes the first contact point and the second contact point having a first electrical parameter.

13. The device of claim 12 wherein the detector includes a voltage source coupled to the first contact point and the second contact point and wherein the first electrical parameter includes a measure of a current.

14. The device of claim 13 wherein the voltage source is configured to supply an increasing potential.

15. The device of claim 12 wherein the detector includes a current source coupled to the first contact point and the second contact point and wherein the first electrical parameter includes a measure of a voltage.

16. The device of claim 15 wherein the current source is configured to supply an increasing current.

17. The device of claim 12 wherein the detector includes a driver circuit configured to deliver an electrical signal and wherein the change in the first physical parameter corresponds to a disbonding of the target molecule and the template molecule.

18. The device of claim 1 wherein at least one of the first surface and the second surface includes at least one of glass, quartz, silicon and a polymer.

19. The device of claim 1 wherein the template molecule is attached to the contact point with at least one of thiol, gold, biotin or streptavidin.

20. A method comprising:
exposing a target molecule to a template molecule to form a hybridized nucleic acid molecule, the template molecule linked between at least two contact points including a first contact point disposed on a first surface and a second contact point disposed on a second surface, wherein the template molecule includes at least one recognition site for a target molecule, wherein a single stranded conductive nucleic acid molecule is selected as the template molecule;
generating an output signal as a function of a change in a first physical parameter indicative of electrical conduction through the template molecule and measured using the first contact point relative to a reference point, wherein the change in the first physical parameter corresponds to an association between the target molecule and the template molecule; and
generating a current or voltage that passes through the first contact point, the template molecule and the second contact point to disassociate the hybridized nucleic acid molecule.

21. The method of claim 20 further including:
monitoring a resonant frequency of the first contact point relative to a reference point;
monitoring a resonant amplitude of the first contact point relative to the reference point;
monitoring a distance between the first contact point and the reference point; and
monitoring an alignment between the first contact point and the reference point.

22. The method of claim 21 wherein the reference point includes the second contact point.

23. The method of claim 20 further including applying an electrical signal to the template molecule to disbond the target molecule.

24. A system comprising:
a target molecule introduction port for receiving a sample;
a sensor having a template molecule in communication with the target molecule introduction port, the template molecule linked between a first point on a first surface and a second point on a second surface, the first surface independent of the second surface and wherein the template molecule has at least one recognition site specific to a target molecule, wherein a single stranded conductive nucleic acid molecule is selected as the template molecule;

a detector coupled to the first point and the second point and configured to generate an output signal based on a change in a measured parameter corresponding to an association between the template molecule with the target molecule, wherein the measured parameter is electrical conduction through the template molecule; and an output circuit to provide a result based on the output signal; and wherein the template molecule, the first contact point, the detector and the second contact point form an electrical circuit, and further, wherein the detector comprises a driving circuit for providing a current or voltage through the electrical circuit for disassociation of the template molecule from the target molecule.

25. The system of claim 24 further including a plurality of sensors, each sensor coupled to the detector by a multiplexer.

26. The system of claim 24 a processor coupled to the detector and having access to a memory, wherein the memory provides data storage for identifying a target molecule based on the change in the measured parameter.

27. The system of claim 24 wherein the output circuit includes at least one of an interface, a display and a wireless transceiver.

28. The system of claim 24 further including a test circuit coupled to the template molecule to determine conductivity of the template molecule.

29. The system of claim 24 further including a reset circuit coupled to the template molecule to disbond a target molecule from the template molecule.

30. The system of claim 24 further including a housing for containment of at least one of the target molecule introduction port, the sensor, the detector and the output circuit.

31. The device of claim 1 wherein an increase in the first physical parameter corresponds to an association between the target nucleic acid molecule and the template nucleic acid molecule.

32. A device comprising:
a template nucleic acid molecule linked between at least two contact points including a first contact point disposed on a first surface and a second contact point disposed on a second surface, wherein the first surface is independent of the second surface, and wherein the template nucleic acid molecule includes at least one recognition site for a target nucleic acid molecule and is selected as a conductive single stranded nucleic acid molecule;

wherein the template nucleic acid molecule, the first contact point, the detector and the second contact point form an electrical circuit, and further, wherein the detector comprises a driving circuit for providing a current or voltage through the electrical circuit for disassociation of the template molecule from the target molecule; and a detector coupled to the first contact point and the second contact point, the first contact point and the second contact point having a first physical parameter indicative of electrical conduction though the template nucleic acid molecule, the detector configured to generate an output signal based on a change in electrical conduction through the template nucleic acid molecule associated with hybridization of a target nucleic acid molecule to the template nucleic acid molecule and with disassociation of the template nucleic acid molecule from the target nucleic acid molecule.

33. The device of claim 32 wherein the first and second surfaces are a fixed distance from each other.

34. A method comprising:
a) exposing a target nucleic acid molecule to a template nucleic acid molecule to yield a hybridized nucleic acid molecule, the template molecule linked between at least two contact points including a first contact point disposed on a first surface and a second contact point disposed on a second surface, wherein the template nucleic acid molecule includes at least one recognition site for the target nucleic acid molecule and is selected as a single stranded conductive nucleic acid molecule;
b) generating an output signal as a function of a change in a first physical parameter indicative of electrical conduction through the template molecule and measured using the first contact point relative to a reference point, wherein the change in the first physical parameter is associated with hybridization of the target nucleic acid molecule to the template nucleic acid molecule; and
c) generating a current or voltage that passes through the first contact point, the template molecule and the second contact point to disassociate the hybridized nucleic acid molecule.

35. The method of claim 34 wherein the change in the first physical parameter is correlated to the percent nucleic acid sequence identity between the target nucleic acid molecule and the template nucleic acid molecule.

36. The device of claim 1 wherein the output signal correlates to the percent nucleic acid sequence identity between the template molecule and the target molecule.

37. The method of claim 20 wherein the output signal correlates to the percent nucleic acid sequence identity between the template molecule and the target molecule.

38. The system of claim 24 wherein the output signal correlates to the percent nucleic acid sequence identity between the template molecule and the target molecule.

* * * * *

SEQUENCE LISTING

<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: A synthetic primer

<400> SEQUENCE: 1
gggtttgatc ctggctcag                                          19

<210> SEQ ID NO 2
<211> LENGTH: 21
<212> TYPE: DNA
<213> ORGANISM: Artificial Sequence
<220> FEATURE:
<223> OTHER INFORMATION: A synthetic primer

<400> SEQUENCE: 2
acggttacct tgttacgact t                                       21

<210> SEQ ID NO 3
<211> LENGTH: 28
<212> TYPE: DNA
<213> ORGANISM: Artificial Sequence
<220> FEATURE:
<223> OTHER INFORMATION: A synthetic primer

<400> SEQUENCE: 3
cgagcggccg cctgggctac acacgtgc                                28

<210> SEQ ID NO 4
<211> LENGTH: 26
<212> TYPE: DNA
<213> ORGANISM: Artificial Sequence
<220> FEATURE:
<223> OTHER INFORMATION: A synthetic primer

<400> SEQUENCE: 4
cgaccgcggc cagcttcacg cagtcg                                  26

<210> SEQ ID NO 5
<211> LENGTH: 121
<212> TYPE: DNA
<213> ORGANISM: Bacillus subtilis

<400> SEQUENCE: 5
ctgggctaca cacgtgctac aatggacaga acaaagggca gcgaaaccgc gaggttaagc    60
caatcccaca atctgttct cagttcggat cgcagtctgc aactcgactg cgtgaagctg   120
g                                                                 121

<210> SEQ ID NO 6
<211> LENGTH: 66
<212> TYPE: DNA
<213> ORGANISM: Bacillus subtilis
<220> FEATURE:
<223> OTHER INFORMATION: A synthetic primer

<400> SEQUENCE: 6
ctgggctaca cacgtgctac aatggacaga acaaagggca gcgaaaccgc gaggttaagc    60
caatcc                                                              66

<210> SEQ ID NO 7
<211> LENGTH: 60
<212> TYPE: DNA
<213> ORGANISM: Artificial Sequence
<220> FEATURE:
<223> OTHER INFORMATION: A synthetic oligonucleotide

<400> SEQUENCE: 7
cacaaatctg ttctcagttc ggatcgcagt ctgcaactcg actgcgtgaa gctgggcatg    60

```
<210> SEQ ID NO 8
<211> LENGTH: 56
<212> TYPE: DNA
<213> ORGANISM: Artificial Sequence
<220> FEATURE:
<223> OTHER INFORMATION: A synthetic oligonucleotide

<400> SEQUENCE: 8
tcgcggtttc gctgcccttt gttctgtcca ttgtagcacg tgtgtagccc agacgt      56

<210> SEQ ID NO 9
<211> LENGTH: 69
<212> TYPE: DNA
<213> ORGANISM: Bacillus subtilis

<400> SEQUENCE: 9
ccagcttcac gcagtcgagt tgcagactgc gatccgaact gagaacagat ttgtgggatt    60
ggcttaacc                                                            69

<210> SEQ ID NO 10
<211> LENGTH: 126
<212> TYPE: DNA
<213> ORGANISM: Artificial Sequence
<220> FEATURE:
<223> OTHER INFORMATION: A synthetic oligonucleotide

<400> SEQUENCE: 10
ctgggctaca cacgtgctac aatggacaga acaaagggca gcgaaaccgc gaggttaagc    60
caatcccaca aatctgttct cagttcggat cgcagtctgc aactcgactg cgtgaagctg   120
ggcatg                                                              126

<210> SEQ ID NO 11
<211> LENGTH: 125
<212> TYPE: DNA
<213> ORGANISM: Artificial Sequence
<220> FEATURE:
<223> OTHER INFORMATION: A synthetic oligonucleotide

<400> SEQUENCE: 11
ccagcttcac gcagtcgagt tgcagactgc gatccgaact gagaacagat ttgtgggatt    60
ggcttaacct cgcggtttcg ctgcccttty ttctgtccat tgtagcacgt gtgtagccca   120
gacgt                                                               125

<210> SEQ ID NO 12
<211> LENGTH: 28
<212> TYPE: DNA
<213> ORGANISM: Artificial Sequence
<220> FEATURE:
<223> OTHER INFORMATION: A synthetic oligonucleotide

<400> SEQUENCE: 12
gatcgatcga tcacagatgc gcgcgcgc                                       28
```